US009951146B2

(12) United States Patent
Allan et al.

(10) Patent No.: US 9,951,146 B2
(45) Date of Patent: Apr. 24, 2018

(54) ANTI-CD20- / ANTI-BAFF BISPECIFIC ANTIBODIES

(71) Applicant: Eli Lilly and Company, Indianapolis, IN (US)

(72) Inventors: Barrett Allan, Encinitas, CA (US); Kristine Kay Kikly, Spiceland, IN (US); Derrick Ryan Witcher, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/079,184

(22) Filed: Mar. 24, 2016

(65) Prior Publication Data
US 2016/0289342 A1 Oct. 6, 2016

Related U.S. Application Data

(60) Provisional application No. 62/142,706, filed on Apr. 3, 2015.

(51) Int. Cl.
A61K 39/395 (2006.01)
C07K 16/46 (2006.01)
C07K 16/28 (2006.01)
C07K 16/24 (2006.01)
A61K 39/00 (2006.01)

(52) U.S. Cl.
CPC .......... *C07K 16/468* (2013.01); *C07K 16/241* (2013.01); *C07K 16/2887* (2013.01); *A61K 2039/505* (2013.01); *C07K 2317/31* (2013.01); *C07K 2317/56* (2013.01); *C07K 2317/565* (2013.01); *C07K 2317/622* (2013.01); *C07K 2317/732* (2013.01); *C07K 2317/734* (2013.01); *C07K 2317/76* (2013.01); *C07K 2317/92* (2013.01); *C07K 2317/94* (2013.01); *C07K 2319/00* (2013.01)

(58) Field of Classification Search
None
See application file for complete search history.

(56) References Cited

U.S. PATENT DOCUMENTS

| 6,403,770 | B1 | 6/2002 | Guo-Liang et al. |
| 6,635,482 | B1 | 10/2003 | Guo-Liang et al. |
| 6,689,579 | B1 | 2/2004 | Guo-Liang et al. |
| 6,716,576 | B1 | 4/2004 | Guo-Liang et al. |
| 6,737,056 | B1 | 5/2004 | Presta |
| 6,812,327 | B1 | 11/2004 | Guo-Liang et al. |
| 7,317,089 | B2 | 1/2008 | Kikly |
| 7,317,091 | B2 | 1/2008 | Lazar et al. |
| 7,485,704 | B2 | 2/2009 | Fahrner et al. |
| 7,605,236 | B2 | 10/2009 | Ruben et al. |
| 7,612,181 | B2 | 11/2009 | Wu et al. |
| 7,807,799 | B2 | 10/2010 | Fahrner et al. |
| 8,153,125 | B2 | 4/2012 | Watkins et al. |
| 2003/0091565 | A1 | 5/2003 | Beltzer et al. |
| 2004/0202658 | A1 | 10/2004 | Benyunes |
| 2005/0186206 | A1 | 8/2005 | Brunetta |
| 2006/0024295 | A1 | 2/2006 | Brunetta |
| 2006/0062787 | A1 | 3/2006 | Hitraya |
| 2009/0068201 | A1 | 3/2009 | Guo-Liang et al. |
| 2009/0148442 | A1 | 6/2009 | Ponce, Jr. et al. |
| 2009/0098129 | A1 | 8/2009 | Rodrigues et al. |
| 2010/0143352 | A1 | 6/2010 | Chan et al. |
| 2012/0070439 | A1 | 3/2012 | Hamblin et al. |
| 2013/0345404 | A1 | 12/2013 | Baurin et al. |
| 2014/0011238 | A1 | 1/2014 | Baurin et al. |
| 2014/0056895 | A1 | 2/2014 | Baurin et al. |
| 2014/0377257 | A1 | 12/2014 | Chan et al. |

FOREIGN PATENT DOCUMENTS

| EP | 1141024 A2 | 7/2000 |
| EP | 1146892 B1 | 10/2001 |
| EP | 1587540 A2 | 7/2004 |
| EP | 1176981 B1 | 11/2005 |
| EP | 1919950 A1 | 2/2006 |
| EP | 1645902 A2 | 4/2006 |
| EP | 1871808 A2 | 10/2006 |
| EP | 2281842 A1 | 2/2011 |
| EP | 2364996 A1 | 9/2011 |
| EP | 2368578 A1 | 9/2011 |
| EP | 2368911 A1 | 9/2011 |
| EP | 1553975 B1 | 1/2012 |
| EP | 2042517 B1 | 11/2012 |
| EP | 2383297 B1 | 1/2013 |

(Continued)

OTHER PUBLICATIONS

Kipriyanov et al., "Bispecific Tandem Diabody for Tumor Therapy with Improved Antigen Binding and Pharmacokinetics", J. Mol. Biol. {1999) 293, 41-56.*
Lin Weiyu, et al, "Dual B cell immunotherapy is superior to individual anti-CD20 depletion or BAFF blockade in murine models of spontaneous or accelerated lupus.", Arthritis & Rheumatology 2015 67(1):215-224.
Byrne Hannah, et al, "A tale of two specificities: bispecific antibodies for therapeutic and diagnostic applications", Trends in Biotechnology, 2013, 31(11): 621-632.

(Continued)

*Primary Examiner* — Ronald B Schwadron

(74) *Attorney, Agent, or Firm* — Robert L. Sharp; Megan N. Thobe

(57) ABSTRACT

Bispecific antibodies are provided that bind CD20 and B-cell Activating Factor of the TNF Family (BAFF) and are characterized as having high affinity and strong simultaneous neutralizing properties to both CD20 and BAFF. The bispecific antibodies of the invention are useful for treating autoimmune diseases including Systemic Lupus Erythematosus, Lupus Nephritis, and primary Sjögren's Syndrome.

2 Claims, No Drawings

(56) References Cited

FOREIGN PATENT DOCUMENTS

| | | | |
|---|---|---|---|
| EP | 2703415 A1 | 3/2014 |
| EP | 2708557 A1 | 3/2014 |
| EP | 1951757 B1 | 5/2014 |
| EP | 2331578 B1 | 6/2014 |
| EP | 2796469 A2 | 10/2014 |
| EP | 2471813 B1 | 12/2014 |
| EP | 2345671 B1 | 11/2015 |
| EP | 2233149 B1 | 2/2016 |
| EP | 2691416 B1 | 5/2016 |
| WO | 1995009917 A1 | 4/1995 |
| WO | 1998018921 A1 | 5/1998 |
| WO | 2000067796 A1 | 11/2000 |
| WO | 2002002641 A1 | 6/2002 |
| WO | 2003016468 A2 | 2/2003 |
| WO | 2004029207 A2 | 4/2004 |
| WO | 2004063351 A2 | 7/2004 |
| WO | 2004099249 A2 | 11/2004 |
| WO | 2005056759 A2 | 6/2005 |
| WO | 2005077981 A2 | 8/2005 |
| WO | 2005092925 A2 | 10/2005 |
| WO | 2005124668 A1 | 12/2005 |
| WO | 2006068867 A1 | 6/2006 |
| WO | 20060085967 A2 | 8/2006 |
| WO | 2007008943 A2 | 1/2007 |
| WO | 2007041635 A2 | 4/2007 |
| WO | 2009052293 A1 | 4/2009 |
| WO | 2010136483 A2 | 12/2010 |
| WO | 2012135345 A1 | 10/2012 |

OTHER PUBLICATIONS

Divi Cornec, et al, "B cells in Sjogren's Syndrome: From pathophysiology to diagnosis and treatment", Journal of Autoimmunity, 2012, 39(3):161-167.

Spiess Christoph, et al, "Alternative molecular formats and therapeutic applications for bispecific antibodies", Molecular Immunology 2015, 67(2): 95-106.

Dimasi, et al, "The Design and characterization of Oligospecific Antibodies for Simultaneous Targeting of Multiple Disease Mediators", Journal of Molecular Biology 2009, 393(3): 672-692.

J Wild, et al, "Neutralization of (NK-cell-derived) B-cell activating factor by Belimumab restores sensitivity of chronic lymphoid Leukemia cells to direct and Rituximab-induced NK lysis", Leukemia 2015, 29(8): 1682.

* cited by examiner

SEQUENCE LISTING

<160> NUMBER OF SEQ ID NOS: 22

<210> SEQ ID NO 1
<211> LENGTH: 715
<212> TYPE: PRT
<213> ORGANISM: Artificial Sequence
<220> FEATURE:
<223> OTHER INFORMATION: First Polypeptide of the exemplified bispecific
      antibody of Table 1

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Gly His
            20                  25                  30

Tyr Trp Ser Trp Ile Arg Gln Pro Pro Gly Lys Cys Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ala Arg Asp Ile Leu Thr Gly Tyr Leu Tyr Tyr Tyr Asp His
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Gly Gly Gly Gly Ser Glu
    130                 135                 140

Ile Val Leu Thr Gln Ser Pro Ala Thr Leu Ser Leu Ser Pro Gly Glu
145                 150                 155                 160

Arg Ala Thr Leu Ser Cys Arg Ala Ser Gln Ser Val Ser Arg Tyr Leu
                165                 170                 175

Ala Trp Tyr Gln Gln Lys Pro Gly Gln Ala Pro Arg Leu Leu Ile Tyr
            180                 185                 190

Asp Ala Ser Asn Arg Ala Thr Gly Ile Pro Ala Arg Phe Ser Gly Ser
        195                 200                 205

```
Gly Ser Gly Thr Asp Ser Thr Leu Thr Ile Ser Ser Leu Glu Pro Glu
            210                 215                 220

Asp Phe Ala Val Tyr Tyr Cys Gln Gln Arg Ser Asn His Pro Arg Thr
225                 230                 235                 240

Phe Gly Cys Gly Thr Lys Val Glu Ile Lys Gly Gly Gly Ser Gly
                245                 250                 255

Gly Gly Gly Ser Gly Gly Gly Ser Glu Val Gln Leu Val Gln Ser
            260                 265                 270

Gly Ala Glu Val Lys Lys Pro Gly Glu Ser Leu Lys Ile Ser Cys Lys
            275                 280                 285

Gly Ser Gly Arg Thr Phe Thr Ser Tyr Asn Met His Trp Val Arg Gln
            290                 295                 300

Met Pro Gly Lys Gly Leu Glu Trp Met Gly Ala Ile Tyr Pro Leu Thr
305                 310                 315                 320

Gly Asp Thr Ser Tyr Asn Gln Lys Ser Lys Leu Gln Val Thr Ile Ser
                325                 330                 335

Ala Asp Lys Ser Ile Ser Thr Ala Tyr Leu Gln Trp Ser Ser Leu Lys
            340                 345                 350

Ala Ser Asp Thr Ala Met Tyr Tyr Cys Ala Arg Ser Thr Tyr Val Gly
            355                 360                 365

Gly Asp Trp Gln Phe Asp Val Trp Gly Lys Gly Thr Thr Val Thr Val
370                 375                 380

Ser Ser Ala Ser Thr Lys Gly Pro Ser Val Phe Pro Leu Ala Pro Ser
385                 390                 395                 400

Ser Lys Ser Thr Ser Gly Gly Thr Ala Ala Leu Gly Cys Leu Val Lys
                405                 410                 415

Asp Tyr Phe Pro Glu Pro Val Thr Val Ser Trp Asn Ser Gly Ala Leu
            420                 425                 430

Thr Ser Gly Val His Thr Phe Pro Ala Val Leu Gln Ser Ser Gly Leu
            435                 440                 445

Tyr Ser Leu Ser Ser Val Val Thr Val Pro Ser Ser Ser Leu Gly Thr
450                 455                 460

Gln Thr Tyr Ile Cys Asn Val Asn His Lys Pro Ser Asn Thr Lys Val
465                 470                 475                 480

Asp Lys Lys Val Glu Pro Lys Ser Cys Asp Lys Thr His Thr Cys Pro
                485                 490                 495

Pro Cys Pro Ala Pro Glu Leu Leu Gly Gly Pro Ser Val Phe Leu Phe
            500                 505                 510

Pro Pro Lys Pro Lys Asp Thr Leu Met Ile Ser Arg Thr Pro Glu Val
            515                 520                 525

Thr Cys Val Val Val Asp Val Ser His Glu Asp Pro Glu Val Lys Phe
530                 535                 540

Asn Trp Tyr Val Asp Gly Val Glu Val His Asn Ala Lys Thr Lys Pro
545                 550                 555                 560

Arg Glu Glu Gln Tyr Asn Ser Thr Tyr Arg Val Val Ser Val Leu Thr
                565                 570                 575

Val Leu His Gln Asp Trp Leu Asn Gly Lys Glu Tyr Lys Cys Lys Val
            580                 585                 590

Ser Asn Lys Ala Leu Pro Ala Pro Glu Glu Lys Thr Ile Ser Lys Gln
            595                 600                 605

Lys Gly Gln Pro Arg Glu Pro Gln Val Tyr Thr Leu Pro Pro Ser Arg
610                 615                 620
```

```
Asp Glu Leu Thr Lys Asn Gln Val Ser Leu Thr Cys Leu Val Lys Gly
625                 630                 635                 640

Phe Tyr Pro Ser Asp Ile Ala Val Glu Trp Glu Ser Asn Gly Gln Pro
                645                 650                 655

Glu Asn Asn Tyr Lys Thr Thr Pro Pro Val Leu Asp Ser Asp Gly Ser
            660                 665                 670

Phe Phe Leu Tyr Ser Lys Leu Thr Val Asp Lys Ser Arg Trp Gln Gln
        675                 680                 685

Gly Asn Val Phe Ser Cys Ser Val Met His Glu Ala Leu His Asn His
        690                 695                 700

Tyr Thr Gln Lys Ser Leu Ser Leu Ser Pro Gly
705                 710                 715

<210> SEQ ID NO 2
<211> LENGTH: 213
<212> TYPE: PRT
<213> ORGANISM: Artificial Sequence
<220> FEATURE:
<223> OTHER INFORMATION: Second Polypeptide of the exemplified
      bispecific antibody of Table 1

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Pro Tyr Ile
            20                  25                  30

His Trp Tyr Gln Gln Lys Pro Gly Gln Ala Pro Arg Leu Leu Ile Tyr
        35                  40                  45

Ala Thr Ser Ala Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Leu Ser His Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 3
<211> LENGTH: 2145
<212> TYPE: DNA
<213> ORGANISM: Artificial Sequence
<220> FEATURE:
<223> OTHER INFORMATION: DNA Seq. Encoding the First Polypeptide of the
      exemplified bispecific antibody of Table 1
```

<400> SEQUENCE: 3

```
caggtgcagc tgcaggagtc gggcccagga ctggtgaagc cttcggagac cctgtccctc    60
acctgcactg tctctggagg ctccttcagt ggtcattact ggagctggat tcgccagccc   120
ccagggaagt gtctggagtg gattggggaa atcaatcata gtggaagcac caactacaac   180
ccgtccctca gagtcgagt caccatatca gtagacacgt ccaagaacca gttctccctg   240
aaactgagct ctgtgaccgc cgcggacacg gctgtgtatt actgtgcgag aggggctaga   300
gatattttga ctggttatct atactactat gaccattggg gccagggaac cctggtcacc   360
gtctcctcag ggggaggggg cagcggagga ggcggatcgg gcggaggagg aagtggaggc   420
ggaggcagcg aaattgtgtt gacgcagtct ccagccaccc tgtctttgtc tcctggggaa   480
agagccaccc tctcctgcag ggccagtcag agtgttagcc gctacttagc ctggtaccag   540
cagaaacctg gccaggctcc caggctcctc atctatgatg catccaacag ggccactggc   600
atcccagcca ggttcagtgg cagtgggtct gggacagact ccactctcac catcagcagc   660
ctagagcctg aagattttgc agtttattac tgtcagcagc gtagcaacca ccctcggacg   720
ttcggctgtg ggaccaaggt ggaaatcaaa ggcggtggtg gcagcggcgg aggcggatcc   780
ggcggaggtg gaagcgaggt gcagctggtg cagtctggag cagaggtgaa aaagcccggg   840
gagtctctga gatctcctg taagggttct ggccgtacat ttaccagtta caatatgcac   900
tgggtgcgcc agatgcccgg gaaaggcctg gagtggatgg gggctattta tcccttgacg   960
ggtgatactt cctacaatca gaagtcgaaa ctccaggtca ccatctcagc cgacaagtcc  1020
atcagcaccg cctacctgca gtggagcagc ctgaaggcct cggacaccgc catgtattac  1080
tgtgcgagat cgacttacgt gggcggtgac tggcagttcg atgtctgggg caaggggacc  1140
acggtcaccg tctcctcagc ctccaccaag ggcccatcgg tcttcccgct agcaccctcc  1200
tccaagagca cctctggggg cacagcggcc ctgggctgcc tggtcaagga ctacttcccc  1260
gaaccggtga cggtgtcgtg gaactcaggc gccctgacca gcggcgtgca caccttcccg  1320
gctgtcctac agtcctcagg actctactcc ctcagcagcg tggtgaccgt gccctccagc  1380
agcttgggca cccagaccta catctgcaac gtgaatcaca agcccagcaa caccaaggtg  1440
gacaagaaag ttgagcccaa atcttgtgac aaaactcaca catgcccacc gtgcccagca  1500
cctgaactcc tggggggacc gtcagtcttc ctcttccccc caaaacctaa ggacaccctc  1560
atgatctccc ggaccctga ggtcacatgc gtggtggtgg acgtgagcca cgaagaccct  1620
gaggtcaagt tcaactggta cgtggacggc gtggaggtgc ataatgccaa gacaaagccg  1680
cgggaggagc agtacaacag cacgtaccgt gtggtcagcg tcctcaccgt cctgcaccag  1740
gactggctga atggcaagga gtacaagtgc aaggtctcca acaaagccct cccagccccc  1800
gaggagaaaa ccatctccaa acagaaaggg cagccccgag aaccacaggt gtacaccctg  1860
cccccatccc gggacgagct gaccaagaac caggtcagcc tgacctgcct ggtcaaaggc  1920
ttctatccca gcgacatcgc cgtggagtgg gagagcaatg ggcagccgga gaacaactac  1980
aagaccacgc cccccgtgct ggactccgac ggctccttct tcctctatag caagctcacc  2040
gtggacaaga gcaggtggca gcaggggaac gtcttctcat gctccgtgat gcatgaggct  2100
ctgcacaacc actacacaca gaagagcctc tccctgtctc cgggt              2145
```

<210> SEQ ID NO 4
<211> LENGTH: 639
<212> TYPE: DNA

<213> ORGANISM: Artificial Sequence
<220> FEATURE:
<223> OTHER INFORMATION: DNA Seq. Encoding the Second Polypeptide of the exemplified bispecific antibody of Table 1

<400> SEQUENCE: 4

```
gaaattgtgt tgacgcagtc tccaggcacc ctgtctttgt ctccagggga aagggccacc    60
ctctcctgca gggccagctc aagtgtaccg tacatccact ggtaccagca gaaacctggc   120
caggctccca ggctcctcat ctatgccaca tccgccctgg cttctggcat cccagacagg   180
ttcagtggca gtgggtctgg gacagacttc actctcacca tcagcagact ggagcctgaa   240
gattttgcag tgtattactg tcagcagtgg ctgagtcatc acccactttt ggccagggg    300 accaagctgg agatcaaacg aactgtggct gcaccatctg tcttcatctt cccgccatct   360
gatgagcagt tgaaatctgg aactgcctct gttgtgtgcc tgctgaataa cttctatccc   420
agagaggcca agtacagtg gaaggtggat aacgccctcc aatcgggtaa ctcccaggag   480
agtgtcacag agcaggacag caaggacagc acctacagcc tcagcagcac cctgacgctg   540
agcaaagcag actacgagaa acacaaagtc tacgcctgcg aagtcaccca tcagggcctg   600
agctcgcccg tcacaaagag cttcaacagg ggagagtgc                          639
```

<210> SEQ ID NO 5
<211> LENGTH: 123
<212> TYPE: PRT
<213> ORGANISM: Artificial Sequence
<220> FEATURE:
<223> OTHER INFORMATION: HCVR1 of the exemplified bispecific antibody of Table 1

<400> SEQUENCE: 5

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Gly His
            20                  25                  30

Tyr Trp Ser Trp Ile Arg Gln Pro Pro Gly Lys Cys Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ala Arg Asp Ile Leu Thr Gly Tyr Leu Tyr Tyr Tyr Asp His
            100                 105                 110

Trp Gly Gln Gly Thr Leu Val Thr Val Ser Ser
        115                 120
```

<210> SEQ ID NO 6
<211> LENGTH: 121
<212> TYPE: PRT
<213> ORGANISM: Artificial Sequence
<220> FEATURE:
<223> OTHER INFORMATION: HCVR2 of the exemplified bispecific antibody of Table 1

<400> SEQUENCE: 6

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Arg Thr Phe Thr Ser Tyr
```

```
                20                  25                  30
Asn Met His Trp Val Arg Gln Met Pro Gly Lys Gly Leu Glu Trp Met
             35                  40                  45

Gly Ala Ile Tyr Pro Leu Thr Gly Asp Thr Ser Tyr Asn Gln Lys Ser
 50                  55                  60

Lys Leu Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
             85                  90                  95

Ala Arg Ser Thr Tyr Val Gly Gly Asp Trp Gln Phe Asp Val Trp Gly
            100                 105                 110

Lys Gly Thr Thr Val Thr Val Ser Ser
            115                 120

<210> SEQ ID NO 7
<211> LENGTH: 106
<212> TYPE: PRT
<213> ORGANISM: Artificial Sequence
<220> FEATURE:
<223> OTHER INFORMATION: LCVR1 of the exemplified bispecific antibody of
      Table 1

<400> SEQUENCE: 7

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Ser Ser Val Pro Tyr Ile
             20                  25                  30

His Trp Tyr Gln Gln Lys Pro Gly Gln Ala Pro Arg Leu Leu Ile Tyr
             35                  40                  45

Ala Thr Ser Ala Leu Ala Ser Gly Ile Pro Asp Arg Phe Ser Gly Ser
 50                  55                  60

Gly Ser Gly Thr Asp Phe Thr Leu Thr Ile Ser Arg Leu Glu Pro Glu
 65                  70                  75                  80

Asp Phe Ala Val Tyr Tyr Cys Gln Gln Trp Leu Ser His Pro Pro Thr
             85                  90                  95

Phe Gly Gln Gly Thr Lys Leu Glu Ile Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: LCVR2 of the exemplified bispecific antibody of
      Table 1

<400> SEQUENCE: 8

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Arg Tyr
             20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Ser Thr Leu Thr Ile Ser Ser Leu Glu Pro
 65                  70                  75                  80

Glu Asp Phe Ala Val Tyr Tyr Cys Gln Gln Arg Ser Asn His Pro Arg
```

```
                    85                  90                  95
Thr Phe Gly Cys Gly Thr Lys Val Glu Ile Lys
            100                 105

<210> SEQ ID NO 9
<211> LENGTH: 13
<212> TYPE: PRT
<213> ORGANISM: Artificial Sequence
<220> FEATURE:
<223> OTHER INFORMATION: HCDR1 of the exemplified bispecific antibody of
      Table 1

<400> SEQUENCE: 9

Lys Gly Ser Gly Arg Thr Phe Thr Ser Tyr Asn Met His
1               5                   10

<210> SEQ ID NO 10
<211> LENGTH: 17
<212> TYPE: PRT
<213> ORGANISM: Artificial Sequence
<220> FEATURE:
<223> OTHER INFORMATION: HCDR2 of the exemplified bispecific antibody of
      Table 1

<400> SEQUENCE: 10

Ala Ile Tyr Pro Leu Thr Gly Asp Thr Ser Tyr Asn Gln Lys Ser Lys
1               5                   10                  15

Leu

<210> SEQ ID NO 11
<211> LENGTH: 14
<212> TYPE: PRT
<213> ORGANISM: Artificial Sequence
<220> FEATURE:
<223> OTHER INFORMATION: HCDR3 of the exemplified bispecific antibody of
      Table 1

<400> SEQUENCE: 11

Ala Arg Ser Thr Tyr Val Gly Gly Asp Trp Gln Phe Asp Val
1               5                   10

<210> SEQ ID NO 12
<211> LENGTH: 13
<212> TYPE: PRT
<213> ORGANISM: Artificial Sequence
<220> FEATURE:
<223> OTHER INFORMATION: HCDR4 of the exemplified bispecific antibody of
      Table 1

<400> SEQUENCE: 12

Thr Val Ser Gly Gly Ser Phe Ser Gly His Tyr Trp Ser
1               5                   10

<210> SEQ ID NO 13
<211> LENGTH: 16
<212> TYPE: PRT
<213> ORGANISM: Artificial Sequence
<220> FEATURE:
<223> OTHER INFORMATION: HCDR5 of the exemplified bispecific antibody of
      Table 1

<400> SEQUENCE: 13

Glu Ile Asn His Ser Gly Ser Thr Asn Tyr Asn Pro Ser Leu Lys Ser
1               5                   10                  15

<210> SEQ ID NO 14
```

```
<211> LENGTH: 17
<212> TYPE: PRT
<213> ORGANISM: Artificial Sequence
<220> FEATURE:
<223> OTHER INFORMATION: HCDR6 of the exemplified bispecific antibody of
      Table 1

<400> SEQUENCE: 14

Ala Arg Gly Ala Arg Asp Ile Leu Thr Gly Tyr Leu Tyr Tyr Tyr Asp
1               5                   10                  15

His

<210> SEQ ID NO 15
<211> LENGTH: 10
<212> TYPE: PRT
<213> ORGANISM: Artificial Sequence
<220> FEATURE:
<223> OTHER INFORMATION: LCDR1 of the exemplified bispecific antibody of
      Table 1

<400> SEQUENCE: 15

Arg Ala Ser Ser Ser Val Pro Tyr Ile His
1               5                   10

<210> SEQ ID NO 16
<211> LENGTH: 8
<212> TYPE: PRT
<213> ORGANISM: Artificial Sequence
<220> FEATURE:
<223> OTHER INFORMATION: LCDR2 of the exemplified bispecific antibody of
      Table 1

<400> SEQUENCE: 16

Tyr Ala Thr Ser Ala Leu Ala Ser
1               5

<210> SEQ ID NO 17
<211> LENGTH: 9
<212> TYPE: PRT
<213> ORGANISM: Artificial Sequence
<220> FEATURE:
<223> OTHER INFORMATION: LCDR3 of the exemplified bispecific antibody of
      Table 1

<400> SEQUENCE: 17

Gln Gln Trp Leu Ser His Pro Pro Thr
1               5

<210> SEQ ID NO 18
<211> LENGTH: 11
<212> TYPE: PRT
<213> ORGANISM: Artificial Sequence
<220> FEATURE:
<223> OTHER INFORMATION: LCDR4 of the exemplified bispecific antibody of
      Table 1

<400> SEQUENCE: 18

Arg Ala Ser Gln Ser Val Ser Arg Tyr Leu Ala
1               5                   10

<210> SEQ ID NO 19
<211> LENGTH: 8
<212> TYPE: PRT
<213> ORGANISM: Artificial Sequence
<220> FEATURE:
<223> OTHER INFORMATION: LCDR5 of the exemplified bispecific antibody of
      Table 1
```

```
<400> SEQUENCE: 19

Tyr Asp Ala Ser Asn Arg Ala Thr
1               5

<210> SEQ ID NO 20
<211> LENGTH: 9
<212> TYPE: PRT
<213> ORGANISM: Artificial Sequence
<220> FEATURE:
<223> OTHER INFORMATION: LCDR6 of the exemplified bispecific antibody of
      Table 1

<400> SEQUENCE: 20

Gln Gln Arg Ser Asn His Pro Arg Thr
1               5

<210> SEQ ID NO 21
<211> LENGTH: 20
<212> TYPE: PRT
<213> ORGANISM: Artificial Sequence
<220> FEATURE:
<223> OTHER INFORMATION: Polypeptide Linker 1 of the exemplified
      bispecific antibody of Table 1

<400> SEQUENCE: 21

Gly Gly Gly Gly Ser Gly Gly Gly Ser Gly Gly Gly Gly Ser Gly
1               5                   10                  15

Gly Gly Gly Ser
            20

<210> SEQ ID NO 22
<211> LENGTH: 15
<212> TYPE: PRT
<213> ORGANISM: Artificial Sequence
<220> FEATURE:
<223> OTHER INFORMATION: Polypeptide Linker 2 of the exemplified
      bispecific antibody of Table 1

<400> SEQUENCE: 22

Gly Gly Gly Gly Ser Gly Gly Gly Gly Ser Gly Gly Gly Gly Ser
1               5                   10                  15
```

ANTI-CD20- / ANTI-BAFF BISPECIFIC ANTIBODIES

The present invention is in the field of medicine, particularly in the novel field of bispecific antibodies directed against CD20 and B-cell Activating Factor of the TNF Family (BAFF). The bispecific antibodies of the present invention are expected to be useful in treating one or more autoimmune diseases having B-cell dysregulation such as Systemic Lupus Erythematosus (SLE), Lupus Nephritis (LN), primary Sjögren's Syndrome (pSS), and/or Grave's Disease (GD).

SLE, LN, and pSS are systemic autoimmune diseases characterized by the development of auto-antibodies. An estimated 30-60% of patients with SLE develop renal involvement (a histological reference indicating progression into LN) at some stage during the course of their disease. LN is a complex, multi-factorial autoimmune disease that, if not controlled, can lead to kidney failure. pSS is characterized by chronic inflammation of the exocrine glands (e.g., salivary and lacrimal glands) and may impact respiratory, vascular, neurological, hepatic, and/or renal functions. There is currently no disease-modifying treatment approved for pSS. Likewise, response to currently available treatments of SLE and LN is slow and often incomplete (with approximately only 25-50% of patients reaching remission).

CD20 is a B-lymphocyte-restricted differentiation antigen expressed by B-cells during early pre-B-cell development. Multiple studies demonstrate CD20 acts as a regulator of B-cell activation, a step required for differentiation of B-cells into plasma cells. Because differentiated B-cells are critical to adaptive immunity, B cell depletion therapy (BCDT) has been explored as a treatment for multiple autoimmune diseases, including SLE and LN. The role played by CD20 in B-cell differentiation lends to the appeal of CD20 as a target for BCDT. However, despite multiple efforts, to date no BCDT targeting CD20 has been approved for the treatment of SLE, LN, or pSS.

BAFF is a cytokine which stimulates B-cell survival, proliferation, and differentiation. Over expression of BAFF has been reported in murine models of autoimmune diseases mimicking SLE, LN, and pSS. Multiple studies suggest that BAFF overexpression associated with autoimmune diseases acts to "rescue" autoreactive B-cells from the deletion pathway. However, anti-BAFF antibody therapies have proven only moderately effective.

Accordingly, there remains a need for alternative therapies for the treatment of SLE, LN, and pSS. Preferably such treatment will be capable of demonstrating efficacy in a large number of patients non-responsive to, or inadequately benefited by, currently available options. One such alternative therapy may include the co-administration of two different bioproducts (e.g., antibodies). Co-administration requires either injections of two separate products or a single injection of a co-formulation of two different antibodies. While two injections permit flexibility of dose amounts and timing, it is inconvenient to patients for compliance, pain, and cost. Additionally, it is often quite challenging or impossible to find co-formulation conditions that permit chemical and physical stability of two different antibodies. Thus, there remains a need for alternative therapies for the treatment of SLE, LN, and pSS, and preferably such alternative therapies will comprise a bispecific antibody.

WO199509917 discloses a method of recombinantly producing bispecific, tetravalent antibodies having dual specificity by producing a single chain variable fragment (scFv) polypeptide fused to a complete antibody (Ab) having a different specificity. U.S. Pat. No. 8,153,125 discloses antibodies directed against human CD20. U.S. Pat. No. 7,317,089 discloses antibodies directed against both soluble and membrane bound forms of human BAFF. However, when following the teachings in WO199509917 to create a starting bispecific antibody comprising the CD20 antibodies of U.S. Pat. No. 8,153,125 and the BAFF antibodies of U.S. Pat. No. 7,317,089, the present inventors discovered significant problems associated with chemical and physical stability. Many modifications were required in the starting bispecific antibody to sufficiently overcome these problems. Neither the need for nor the actual changes are suggested in the art. Further, the several changes are not routine or derived from common general knowledge. Likewise, the single antibodies themselves did not have these problems, suggesting that the local environment around these amino acid domains differed in the context of bispecific antibodies. Thus, pharmacological intervention with a bispecific antibody that neutralizes both CD20 and BAFF is needed.

The present invention provides a bispecific antibody having four polypeptide chains, two first polypeptide chains and two second polypeptide chains, wherein each first polypeptide chain comprises a single chain variable fragment (scFv) independently linked at the N-terminus of a mAb IgG heavy chain (HC) via a polypeptide linker (L1) and each of the second polypeptide chains comprises a mAb light chain (LC). According to bispecific antibodies of the present invention, each HC comprises a heavy chain variable region (HCVR1) with heavy chain complementarity determining regions (HCDRs) 1-3 and each LC comprises a light chain variable region (LCVR1) with light chain complementarity determining regions (LCDRs) 1-3. Additionally, according to bispecific antibodies of the present invention, each scFv comprises a light chain variable region (LCVR2) with LCDRs 4-6 and a heavy chain variable region (HCVR2) with HCDRs 4-6. Also, according to bispecific antibodies of the present invention, LCVR2 is linked at its C-terminus to L1 and linked at its N-terminus to a polypeptide linker (L2) which is linked to the C-terminus of HCVR2.

According to particular embodiments of bispecific antibodies of the present invention, the amino acid sequence of HCDR1 is given by SEQ ID NO:9, the amino acid sequence of HCDR2 is given by SEQ ID NO:10, the amino acid sequence of HCDR3 is given by SEQ ID NO:11, the amino acid sequence of LCDR1 is given by SEQ ID NO:15, the amino acid sequence of LCDR2 is given by SEQ ID NO:16, the amino acid sequence of LCDR3 is given by SEQ ID NO:17, the amino acid sequence of HCDR4 is given by SEQ ID NO:12, the amino acid sequence of HCDR5 is given by SEQ ID NO:13, the amino acid sequence of HCDR6 is given by SEQ ID NO:14, the amino acid sequence of LCDR4 is given by SEQ ID NO:18, the amino acid sequence of LCDR5 is given by SEQ ID NO:19, and the amino acid sequence of LCDR6 is given by SEQ ID NO:20.

According to particular embodiments, the HC comprises a mAb IgG1 isotype. In some embodiments, bispecific antibodies of the present invention include one or more modifications in the constant region of each HC that enhance effector function. Even more particular embodiments include the amino acid glutamic acid at residue 601 and glutamine at residue 608 (residue numbering based on the first polypeptide of the exemplified bispecific antibody of Table 1).

According to further particular embodiments, each LC comprises a mAb kappa light chain. In some such embodiments, the amino acid sequence of LCVR1 is given by SEQ ID NO:7, and the amino acid sequence of LCVR2 is given by SEQ ID NO:8. According to further particular embodiments the amino acid sequence of HCVR1 is given by SEQ ID NO:5 and the amino acid sequence of HCVR2 is given by SEQ ID NO:6. According to even further embodiments, the amino acid sequence of L1 is given by SEQ ID NO:21 and the amino acid sequence of L2 is given by SEQ ID NO:22. In an even more particular embodiment of a bispecific antibody of the present invention, the amino acid sequence of each of the first polypeptides is given by SEQ ID NO:1 and the amino acid sequence of each of the second polypeptides is given by SEQ ID NO:2.

The present invention also relates to nucleic acid molecules and expression vectors encoding bispecific antibodies of the present invention. In an embodiment, the present invention provides a DNA molecule comprising a polynucleotide sequence encoding the first polypeptide, wherein the amino acid sequence of the first polypeptide is SEQ ID NO:1. In an embodiment, the present invention also provides a DNA molecule comprising a polynucleotide sequence encoding the second polypeptide, wherein the amino acid sequence of the second polypeptide is SEQ ID NO:2. In a further embodiment, the present invention provides a DNA molecule comprising a polynucleotide sequence encoding the first polypeptide having the amino acid sequence of SEQ ID NO:1, and comprising a polynucleotide sequence encoding the second polypeptide having the amino acid sequence of SEQ ID NO:2. In a particular embodiment the polynucleotide sequence encoding the first polypeptide having the amino acid sequence of SEQ ID NO:1 is given by SEQ ID NO:3 and the polynucleotide sequence encoding the second polypeptide having the amino acid sequence of SEQ ID NO:2 is given by SEQ ID NO:4.

The present invention also provides a mammalian cell transformed with DNA molecule(s) which cell is capable of expressing a bispecific antibody comprising the first polypeptide and the second polypeptide of the present invention. Also, the present invention provides a process for producing a bispecific antibody comprising the first polypeptide and the second polypeptide, comprising cultivating the mammalian cell under conditions such that a bispecific antibody of the present invention is expressed. The present invention also provides a bispecific antibody produced by said process.

The present invention also provides a method of treating an autoimmune disease having B-cell dysregulation, such as SLE, LN, pSS, or GD comprising administering to a patient in need thereof an effective amount of a bispecific antibody of the present invention.

The present invention also provides a bispecific antibody of the present invention for use in therapy. More particularly, the present invention provides a bispecific antibody of the present invention for use in the treatment of SLE, LN, pSS, or GD.

The present invention also provides a pharmaceutical composition comprising a bispecific antibody of the present invention and one or more pharmaceutically acceptable carriers, diluents, or excipients. Pharmaceutical compositions of the present invention can be used in the treatment of SLE, LN, pSS, or GD, whereby such treatment comprises administering to a patient in need thereof pharmaceutical compositions of the present invention.

In an embodiment, the present invention also provides the use of a bispecific antibody of the present invention in the manufacture of a medicament for the treatment of SLE, LN, pSS, or GD.

As referred to herein, the term "bispecific antibody" refers to an engineered polypeptide comprising four antigen binding sites. Two of the four antigen binding sites bind CD20 and the other two antigen binding sites bind BAFF. A bispecific antibody of the present invention is capable of binding CD20 and BAFF alone or simultaneously, and neutralizes at least one human CD20 bioactivity and at least one human BAFF bioactivity in vitro and/or in vivo. The bispecific antibodies of the present invention are also potent inhibitors of CD20 in the presence or absence of BAFF in vitro.

Also, a bispecific antibody, as referred to herein, comprises four polypeptide chains, two first polypeptides and two second polypeptides. Each of the first polypeptides is engineered to comprise a single chain variable fragment (scFv) linked at the N-terminus of a mAb heavy chain (HC) by a polypeptide linker (L1). Each of the second polypeptides is engineered to comprise a mAb light chain (LC) and form inter-chain disulfide bonds with one of the first polypeptides, specifically within the HC of a first polypeptide. Each first polypeptide is engineered to form inter-chain disulfide bonds with the other first polypeptide, specifically between the HC of each of the first polypeptides. Each first polypeptide is further engineered to form intra-chain disulfide bonds, specifically within the scFv of each respective first polypeptide.

As referred to herein, a "single chain variable fragment" (scFv) of a first polypeptide, refers to a polypeptide chain comprising a heavy chain variable region (HCVR2) and a light chain variable region (LCVR2) linked via a polypeptide linker (L2). Additionally, as referred to herein (and as represented in the following schematic), the LCVR2 of each scFv is: a.) linked, at its C-terminus, to the N-terminus of one HC (of a first polypeptide) by a polypeptide linker (L1); and b.) linked, at its N-terminus, to the C-terminus of the HCVR2 of the same scFv via a second polypeptide linker (L2).

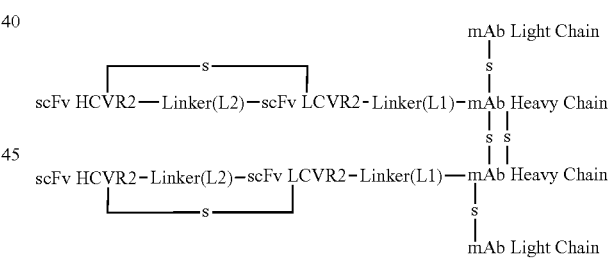

According to bispecific antibodies of the present invention, the HC of each first polypeptide is classified as gamma, which defines the isotype (e.g., as an IgG). The isotype may be further divided into subclasses (e.g., $IgG_1$, $IgG_2$, $IgG_3$, and $IgG_4$). In particular embodiments, bispecific antibodies of the present invention are IgG1. The C-terminal portion of each HC defines a constant region (CH) primarily responsible for effector function. In particular embodiments, bispecific antibodies of the present invention have one or more modifications in the CH of each HC that enhances effector function. In more particular embodiments, bispecific antibodies of the present invention are IgG1 and have modifications in the CH of both HCs that enhance effector function. In even more particular embodiments, such modifications include the amino acid glutamic acid at residue 601 and glutamine at residue 608 in the CH of both HCs (residue numbering based on the first polypeptide of the exemplified bispecific antibody of Table 1). The N-terminal portion of each HC of each first polypeptide includes a variable region (HCVR1).

Additionally, according to bispecific antibodies of the present invention each mAb light chain (LC), comprising the second polypeptide, is classified as kappa or lambda and characterized by a particular constant region as known in the art. In particular embodiments the bispecific antibodies of the present invention comprise kappa LCs. The C-terminal portion of each LC defines a light chain constant region, whereas the N-terminal portion of each LC of each second polypeptide includes a light chain variable region (LCVR1).

The HCVR1 and LCVR1, of each HC and LC respectively, and HCVR2 and LCVR2, of each scFv, can be further subdivided into regions of hypervariability, termed complementarity determining regions (CDRs), interspersed with regions that are more conserved, termed framework regions (FR). Preferably, the framework regions of the bispecific antibodies of the invention are of human origin or substantially of human origin. Each HCVR1, HCVR2, LCVR1 and LCVR2 of bispecific antibodies according to the present invention are composed of three CDRs and four FRs, arranged from amino-terminus to carboxy-terminus in the following order: FR1, CDR1, FR2, CDR2, FR3, CDR3, FR4. Herein the 3 CDRs of each HCVR1 are referred to as "HCDR1, HCDR2 and HCDR3;" the 3 CDRs of each HCVR2 are referred to as "HCDR4, HCDR5 and HCDR6;" the 3 CDRs of each LCVR1 are referred to as "LCDR1, LCDR2 and LCDR3;" and the 3 CDRs of each LCVR2 are referred to as "LCDR4, LCDR5 and LCDR6." The CDRs contain most of the residues which form specific interactions with the antigen. The functional ability of a bispecific antibody of the present invention to bind a particular antigen is largely influenced by the six CDRs.

As used interchangeably herein, "antigen-binding portion," "antigen-binding site," and "antigen-binding region" refers to those portions of bispecific antibodies of the present invention which contain the amino acid residues that interact with an antigen and confer to the bispecific antibody specificity and affinity for a respective antigen. According to bispecific antibodies of the present invention, antigen-binding sites are formed by HCVR1/LCVR1 pairs (of a LC and HC bound by inter-chain disulfide bonds) and by a scFv HCVR2/LCVR2 pair. Additionally, according to bispecific antibodies of the present invention, antigen-binding sites formed by each HCVR1/LCVR1 pair are the same (e.g., comprises specificity and affinity for a same antigen), and antigen-binding sites formed by each scFv HCVR2/LCVR2 pair are the same (e.g., comprises specificity and affinity for a same antigen). However, according to bispecific antibodies of the instant invention, antigen-binding sites formed by each HCVR1/LCVR1 pair are different (e.g., comprises specificity and affinity for a different antigen) from antigen-binding sites formed by each scFv HCVR2/LCVR2 pair.

A "parent antibody" or "parental antibody," as used interchangeably herein, is an antibody encoded by an amino acid sequence which is used for preparation of one of the mAb (e.g., both HCs and LCs) and scFv of the bispecific antibody, for example through amino acid substitutions and structural alteration. The parent antibody may be a murine, chimeric, humanized, or human antibody. Initial attempts in constructing a bispecific antibody according to the present invention included constructs in which a parental BAFF antibody (such as described in U.S. Pat. No. 7,317,089) was engineered to comprise a scFv portion in various configurations and orientations, and a parental CD20 antibody (such as described in U.S. Pat. No. 8,153,125) was engineered to comprise both a scFV as well as mAb portion of the bispecific antibody.

The terms "Kabat numbering" or "Kabat labeling" are used interchangeably herein. These terms, which are recognized in the art, refer to a system of numbering amino acid residues which are more variable (i.e., hypervariable) than other amino acid residues in the heavy chain and light chain variable regions of an antibody (Kabat, et al., *Ann. NY Acad. Sci.* 190:382-93 (1971); Kabat et al., *Sequences of Proteins of Immunological Interest*, Fifth Edition, U.S. Department of Health and Human Services, NIH Publication No. 91-3242 (1991)).

The terms "North numbering" or "North labeling" are used interchangeably herein. These terms, which are recognized in the art, refer to a system of numbering amino acid residues which are more variable (i.e., hypervariable) than other amino acid residues in the heavy and light chains variable regions of an antibody and is based, at least in part, on affinity propagation clustering with a large number of crystal structures, as described in (North et al., *A New Clustering of Antibody CDR Loop Conformations*, Journal of Molecular Biology, 406:228-256 (2011).

The relationship of the various regions and linkers are exemplified, in an exemplified bispecific antibody of the present invention, in Table 1 (numbering of amino acids applies linear numbering; assignment of amino acids to variable domains is based on the International Immunogenetics Information System® available at www.imgt.org; assignment of amino acids to CDR domains is based on the well-known Kabat and North numbering conventions and is reflected at the end of Table 1):

TABLE 1

Amino acid regions of an exemplified bispecific antibody of the present invention.

| SEQ ID NO: 1 | | | SEQ ID NO: 2 | | |
|---|---|---|---|---|---|
| Exemplified HCVR2 (BAFF) | Region | Positions | | | |
| | FRH1-1 | 1-22 | | | |
| | HCDR4 | 23-35 | | | |
| | FRH1-2 | 36-49 | | | |
| | HCDR5 | 50-65 | | | |
| | FRH1-3 | 66-95 | | | |
| | HCDR6 | 96-112 | | | |
| | FRH1-4 | 113-123 | | | |
| Exemplified Linker | L2 | 124-143 | | | |
| Exemplified LCVR2 (BAFF) | FRL1-1 | 144-166 | | | |
| | LCDR4 | 167-177 | | | |
| | FRL1-2 | 178-191 | | | |
| | LCDR5 | 192-199 | | | |
| | FRL1-3 | 200-231 | | | |
| | LCDR6 | 232-240 | | | |
| | FRL1-4 | 241-250 | | | |
| Exemplified Linker | L1 | 251-265 | Exemplified LCVR1 (CD20) | Region | Positions |
| Exemplified HCVR1 (CD20) | FRH1 | 266-287 | | FRL1 | 1-23 |
| | HCDR1 | 288-300 | | LCDR1 | 24-33 |
| | FRH2 | 301-314 | | FRL2 | 34-47 |
| | HCDR2 | 315-331 | | LCDR2 | 48-55 |
| | FRH3 | 332-361 | | FRL3 | 56-87 |
| | HCDR3 | 362-375 | | LCDR3 | 88-96 |
| | FRH4 | 376-386 | | FRL4 | 97-106 |
| Exemplified Constant Region | CH | 387-715 | Exemplified Constant Region | CL | 107-213 |
| CDR | Starting Amino Acid Pos. Definition | | | Ending Amino Acid Pos. Definition | |
| HCDR1 | North | | | Kabat | |
| HCDR2 | Kabat | | | Kabat | |
| HCDR3 | North | | | Kabat | |

TABLE 1-continued

Amino acid regions of an exemplified bispecific antibody of the present invention.

| | SEQ ID NO: 1 | SEQ ID NO: 2 |
|---|---|---|
| HCDR4 | North | Kabat |
| HCDR5 | Kabat | Kabat |
| HCDR6 | North | Kabat |
| LCDR1 | Kabat | Kabat |
| LCDR2 | North | Kabat |
| LCDR3 | Kabat | Kabat |
| LCDR4 | Kabat | Kabat |
| LCDR5 | North | Kabat |
| LCDR6 | Kabat | Kabat |

The exemplified bispecific antibody of the present invention in Table 1 comprises two first polypeptides having amino acid sequences of SEQ ID NO:1 and two second polypeptides having amino acid sequences of SEQ ID NO:2. According to the exemplified bispecific antibody of the present invention presented in Table 1, each of the first polypeptides forms an inter-chain disulfide bond with each of the second polypeptides between cysteine residue 489 of SEQ ID NO:1 and cysteine residue 213 of SEQ ID NO:2; at least two inter-chain disulfide bonds with the other first polypeptide, the first inter-chain disulfide bond forming between cysteine residue 495 (of SEQ ID NO:1) of the first polypeptide and cysteine residue 495 (of SEQ ID NO:1) of the other first polypeptide, the second inter-chain disulfide bond forming between cysteine residue 498 (of SEQ ID NO:1) of the first polypeptide and cysteine residue 498 (of SEQ ID NO:1) of the other first polypeptide; and an intra-chain disulfide bond formed in the scFv of each first polypeptide between cysteine residue 44 (of SEQ ID NO:1) and cysteine residue 243 (of SEQ ID NO:1) of each respective first polypeptide. Further, the exemplified bispecific antibody of Table 1 is glycosylated at asparagine residue 566 of SEQ ID NO:1 of both first polypeptides.

Bispecific Antibody Engineering

Significant problems associated with chemical and physical stability were encountered when constructing a bispecific antibody of the present invention. Problems encountered included poor expression, splice variant formation, poor purification recovery, low thermosability, aggregation of expressed bispecific antibodies, misfolding of scFv, LC clipping, low binding affinity and low target neutralization activity, poor solubility, and rapid clearance in vivo.

For example, initial attempts in constructing a bispecific antibody according to the present invention included constructs in which a parental CD20 antibody (described in U.S. Pat. No. 8,153,125) comprised the mAb antibody portion and a parental BAFF antibody (such as described in U.S. Pat. No. 7,317,089) comprised the scFv portions of the bispecific antibody. Initial constructs included the scFv portion being conjugated to the mAb portion in various configurations, including at the amino-terminus or the carboxyl terminus for both HCs and LCs, respectively. Additionally, initial constructs included the scFv portion varying in arrangement of the HCVR2 and LCVR2 (e.g., mAb portion (C or N terminus)-linker 1-LCVR2 or HCVR2-linker 2-the other of LCVR2 or HCVR2). Further, parental BAFF antibody constructs included combinations of heavy chain germline frameworks VH4-59 and VH4-34, and light chain germline framework L6. Parental CD20 antibody constructs also included combinations of heavy chain germline framework VH5-51 and light chain germline framework A27. Parental CD20 antibody constructs also included both HCs having an IgG1 subclass, as well as, modifications within the constant region (CH) of each HC (of IgG1 subclass), for example, as described in U.S. Pat. No. 8,153,125. Initial constructs were cloned into a human IgG1-Fc mammalian expression vector and expressed in HEK293F cells. However, initially produced bispecific constructs as (described above) exhibited one or more of the chemical and/or physical problem(s) described above.

Structural modifications were therefore made to address the significant chemical and physical stability problems associated with attempting to construct a bispecific antibody of the present invention. For example, modifications, relative to the parental BAFF antibody, were engineered in HCDR4, HCDR5, LCDR4, LCDR5, and LCDR6. Additionally, constructed HCVR2 and LCVR2 were engineered into a BAFF scFv format according to the following formula: HCVR2-L2-LCVR2-L1-(N-term.) HC (CD20). A disulfide bond, for stabilizing BAFF scFv, was engineered between HCVR2 (G44C) and LCVR2 (G243C) (amino acid residue numbering based on exemplified bispecific antibody of Table 1). Additionally, the heavy chain germline framework was changed, relative to the parental BAFF antibody, from HC4-59 to HC4-34. The mAb portion of the bispecific antibody of the present invention was also engineered to address chemical and physical stability problems (described above), including binding affinity and neutralization of CD20. For example, modifications relative to the parental CD20 antibody were engineered in LCDR3 and the CH of the HC (specifically the CH2 region of the HC IgG1 backbone).

Further, electrostatic surface charge of the bispecific antibody was calculated and charged patches were identified and disrupted. Extensive stability studies were performed and the constructed bispecific antibodies were screened for thermostability and physical and chemical stability properties as well as BAFF and CD20 binding and neutralizing properties relative to the respective parental antibodies.

Nucleic acid sequence, encoding engineered BAFF scFv construct and CD20 mAb construct (comprising the extensive chemical and physical modifications and oriented in the manner described herein), was engineered into an IgG1 expression vector for expression by mammalian cells such as CHO and HEK293. Following initial expression of bispecific antibody of the present invention, splice variant sites were identified. Splice variant issues were eliminated through introduction of engineered silent modifications to the nucleic acid sequence, which was re-engineered into an IgG1 expression vector for expression by mammalian cells such as CHO and HEK293.

Expressed bispecific antibodies of the present invention were extensively screened for chemical and physical stability properties, as well as functional properties including BAFF and CD20 binding affinity and neutralization properties.

A bispecific antibody engineered to include a CD20 mAb with a modified IgG1 subclass (relative to native IgG1: I601E, A608Q) and a CDR modification (relative to the parental CD20 antibody: LCDR3 at N93H), as well as BAFF scFv with seven CDR modifications (relative to the parental BAFF antibody: HCVR at Y32H, Y99A, Y100R, Y107L, F110Y, and Y112H, LCVR at W237H) and modified HC framework (relative to parental BAFF antibody: VH4-34→VH4-39), when orientated as described herein, was identified as improving the expression, physical stability, chemical stability, thermostability, and affinity and neutralization issues (described above) demonstrated in initial constructs (amino acid residue numbering based on exemplified bispecific antibody of Table 1). Additionally, these engineered modifications resulted in an improved rate of clearance in cynomolgus monkeys. None of the above modifications are routine or common general knowledge suggested in the art and the need for these modifications was not identified in initial characterizations of the individual parental antibodies.

Bispecific Antibody Expression

Expression vectors capable of directing expression of genes to which they are operably linked are well known in the art. Expression vectors can encode a signal peptide that facilitates secretion of the polypeptide(s) from a host cell. The signal peptide can be an immunoglobulin signal peptide or a heterologous signal peptide. The first polypeptide chain and the second polypeptide chain may be expressed independently from different promoters to which they are operably linked in one vector or, alternatively, the first and second polypeptide chains may be expressed independently from different promoters to which they are operably linked in two vectors—one expressing the first polypeptide chain and one expressing the second polypeptide chain.

A host cell includes cells stably or transiently transfected, transformed, transduced, or infected with one or more expression vectors expressing a first polypeptide chain, a second polypeptide chain or both a first and a second polypeptide chain of the invention. Creation and isolation of host cell lines producing a bispecific antibody of the invention can be accomplished using standard techniques known in the art. Mammalian cells are preferred host cells for expression of bispecific antibodies. Particular mammalian cells are CHO and HEK 293. Preferably, the bispecific antibodies are secreted into the medium in which the host cells are cultured, from which the bispecific antibodies can be recovered or purified by conventional techniques. For example, the medium may be applied to and eluted from a Protein A or G column using conventional methods. Additionally, soluble aggregate and multimers may be effectively removed by common techniques, including size exclusion, hydrophobic interaction, ion exchange, or hydroxyapatite chromatography. The product may be immediately frozen, for example at −70° C., or may be lyophilized.

It is well known in the art that mammalian expression of antibodies results in glycosylation. Typically, glycosylation occurs in the Fc region of the antibody at a highly conserved N-glycosylation site. N-glycans typically attach to asparagine. By way of example, each HC of the exemplified bispecific antibody presented in Table 1 is glycosylated at asparagine residue 566 of SEQ ID NO:1.

Therapeutic Uses

As used herein, "treatment" and/or "treating" are intended to refer to all processes wherein there may be a slowing, interrupting, arresting, controlling, or stopping of the progression of the disorders described herein, but does not necessarily indicate a total elimination of all disorder symptoms. Treatment includes administration of a bispecific antibody of the present invention for treatment of a disease or condition in a patient that would benefit from a decreased level of CD20 positive B cells and/or BAFF or decreased bioactivity of CD20 positive B cells and/or BAFF, and includes: (a) inhibiting further progression of the disease, i.e., arresting its development; and (b) relieving the disease, i.e., causing regression of the disease or disorder or alleviating symptoms or complications thereof. The bispecific antibody of the present invention is expected to treat an autoimmune disease having B-cell dysregulation, including SLE, LN, pSS, and/or GD.

The terms "patient," "subject," and "individual," used interchangeably herein, refer to a human. In certain embodiments, the patient is further characterized with a disease, disorder, or condition (e.g., an autoimmune disorder) that would benefit from a decreased level or decreased bioactivity of both CD20 positive B cells and BAFF. In another embodiment the patient is further characterized as being at risk of developing a disorder, disease, or condition that would benefit from a decreased level or decreased bioactivity of both CD20 positive B cells and BAFF.

Pharmaceutical Composition

A bispecific antibody of the invention can be incorporated into a pharmaceutical composition suitable for administration to a patient. A bispecific antibody of the invention may be administered to a patient alone or with a pharmaceutically acceptable carrier and/or diluent in single or multiple doses. Such pharmaceutical compositions are designed to be appropriate for the selected mode of administration, and pharmaceutically acceptable diluents, carrier, and/or excipients such as dispersing agents, buffers, surfactants, preservatives, solubilizing agents, isotonicity agents, stabilizing agents and the like are used as appropriate. Said compositions can be designed in accordance with conventional techniques disclosed in, e.g., Remington, *The Science and Practice of Pharmacy*, 19$^{th}$ Edition, Gennaro, Ed., Mack Publishing Co., Easton, Pa. 1995 which provides a compendium of formulation techniques as are generally known to practitioners. Suitable carriers for pharmaceutical compositions include any material which, when combined with a bispecific antibody of the invention, retains the molecule's activity and is non-reactive with the patient's immune system. A pharmaceutical composition of the present invention comprises a bispecific antibody and one or more pharmaceutically acceptable carriers, diluents, or excipients.

A pharmaceutical composition comprising a bispecific antibody of the present invention can be administered to a patient at risk for or exhibiting diseases or disorders as described herein using standard administration techniques.

A pharmaceutical composition of the invention contains an effective amount of a bispecific antibody of the invention. An effective amount refers to an amount necessary (at dosages and for periods of time and for the means of administration) to achieve the desired therapeutic result. An effective amount of the bispecific antibody may vary according to factors such as the disease state, age, sex, and weight of the individual, and the ability of the antibody or antibody portion(s) to elicit a desired response in the individual. An effective amount is also one in which any toxic or detrimental effect of the bispecific antibody is outweighed by the therapeutically beneficial effects.

EXAMPLES

Except as noted otherwise, the exemplified engineered bispecific antibody referred to throughout the Examples refers to the exemplified bispecific antibody of the present invention presented in Table 1 above.

Bispecific Antibody Expression and Purification

The exemplified bispecific antibody is expressed and purified essentially as follows. A glutamine synthetase (GS) expression vector containing the DNA of SEQ ID NO:3 (encoding the exemplified first polypeptide chain of SEQ ID NO:1) and SEQ ID NO:4 (encoding the exemplified second polypeptide chain of SEQ ID NO:2) is used to transfect a Chinese hamster cell line (CHO, GS knockout clone 1D3), by electroporation. The expression vector encodes a SV Early (Simian Virus 40E) promoter and the gene for GS.

Expression of GS allows for the biochemical synthesis of glutamine, an amino acid required by the CHO cells. Post-transfection, cells undergo bulk selection with 50 μM L-methionine sulfoximine (MSX). The inhibition of GS by MSX is utilized to increase the stringency of selection. Cells with integration of the expression vector cDNA into transcriptionally active regions of the host cell genome can be selected against CHO wild type cells, which express an endogenous level of GS. Transfected pools are plated at low density to allow for close-to-clonal outgrowth of stable expressing cells. The masterwells are screened for bispecific antibody expression and then scaled up in serum-free, suspension cultures to be used for production. Clarified medium, into which the exemplified bispecific antibody has been secreted, is applied to a Protein A affinity column that has been equilibrated with a compatible buffer such as phosphate buffered saline (pH 7.4). The column is washed to remove nonspecific binding components. The bound bispecific antibody is eluted, for example, by pH gradient (such as 0.1 M sodium phosphate buffer pH 6.8 to 0.1 M sodium citrate buffer pH 2.5) and neutralized with Tris, pH 8 buffer. Bispecific antibody fractions are detected, such as by SDS-PAGE or analytical size-exclusion, and then are pooled. Soluble aggregate and multimers may be effectively removed by common techniques including size exclusion, hydrophobic interaction, ion exchange, or hydroxyapatite chromatography. The bispecific antibody is concentrated and/or sterile filtered using common techniques. The purity of the exemplified bispecific antibody after these chromatography steps is greater than 98% (monomer). The bispecific antibody may be immediately frozen at −70° C. or stored at 4° C. for several months.

Bispecific Antibody Binding Affinity to CD20

Binding affinity and stoichiometry of the exemplified bispecific antibody to human CD20 is measured by Meso Scale Discovery based solution equilibrium titration method (MSD-SET) using a MSD SI6000 instrument (Meso Scale Discovery, Rockville, Md.). Multi-array 96-well assay plates (Meso Scale Discovery, p/n. L15XA-3) are coated with 0.5 μg/mL of a goat anti-human Fc capture antibody (Jackson ImmunoResearch, p/n. 109-005-098) in PBS and are incubated overnight at 4° C. Following incubation, the plates are washed with PBS and then blocked using 3% Blocker A solution (Meso Scale Discovery, p/n. R93AA-1) for 60 minutes at room temperature. The plates are then washed again with PBS.

Exemplified bispecific antibody samples are prepared in duplicate at one of 500 μM or 25 μM. Fixed WIL2-S cells (human B-lymphoma cells that express CD20, ATCC CRL-8885) are pelleted by centrifugation (500×G for 4 minutes at 10° C.), the supernatant is discarded and the pellet is resuspended in 3% Blocker A solution at a concentration of 400 million cells/mL. Cells are serially diluted (using 3-fold dilutions) in a V-bottom 96-well plate with 3% Blocker A solution down to 7000 cells/mL (creating a total of 11 cellular concentrations for each bispecific antibody concentration replicate). A blank (no cells/mL) sample is also created for inclusion in the titration curve (creating a 12$^{th}$ concentration for each replicate).

Exemplified bispecific antibody (diluted in 3% Blocker A solution to either 1 nM or 50 pM) is mixed, at a 1:1 ratio, with each of the 11 different cellular concentrations and blank of each replicate (final concentration for exemplified bispecific antibody is 500 nM or 25 pM; final concentration of WIL2-S cells is approx. 200 million cells/mL to approx. 3500 cells/mL). Mixtures are incubated, on a plate shaker, overnight at 37° C. and then pelleted by centrifugation (500×G for 4 minutes at 10° C.). Following centrifugation, 50 μL is added to wells of the MSD multi-array 96-well assay plates previously coated with goat anti-human Fc capture antibody and incubated for 60 minutes at room temperature on a plate shaker. Plates are then washed with PBS. Thereafter, 25 μL of 1 μg/mL SULFO-TAG conjugated anti-human/NHP kappa light chain secondary antibody (Meso Scale Discovery, p/n. D20TF-6) in 1% Blocker A solution is added to each well. Plates are then incubated, on a plate shaker, at room temperature for 60 minutes and are then washed with PBS three times. 1× Read Buffer T (Meso Scale Discovery, p/n. R92TC-1) is added to each well and plates are read on a MSDSI6000 plate reader (Meso Scale Discovery, Rockville Md.). Data is exported to the KinExA Pro Software (Sapidyne Instruments, Inc., Boise Id.) and results are fit to the "Affinity, Standard Constant Partner (Calculate TCM)" model to determine $K_D$.

The above assay is also performed in the presence of saturating amounts of human BAFF, where the concentration of exemplified bispecific antibody (after mixing with the 11 different cellular concentrations) is held at one of 100 μM or 2 nM and human BAFF is added in 10-fold molar excess (1 nM and 20 nM trimer concentrations, respectively).

The binding affinity of the exemplified bispecific antibody to human CD20 (not in presence of saturating human BAFF) (N=3), determined substantially as described herein, is $K_D$=239±68 μM (Avg.±SD). The binding affinity of the exemplified bispecific antibody to human CD20 (in presence of saturating human BAFF) (N=3), determined substantially as described herein, is $K_D$=305±133 μM (Avg.±SD). These results demonstrate that the exemplified bispecific antibody of the present invention produces a binding response (dependent upon the concentration of bispecific antibody) with human CD20 in the presence or absence of saturating concentrations of recombinant human BAFF.

Bispecific Antibody Binding Affinity to BAFF

Binding affinity and stoichiometry of the exemplified bispecific antibody to human BAFF is measured by MSD-SET using purified recombinant human soluble BAFF (expressed from HEK293 cells). Purified recombinant BAFF is biotinylated using EZ-Link Sulfo-NHS-LC biotin reagent (Thermo Scientific, p/n. 21335). In vitro Biacore assays (data not shown), demonstrate that native and biotinylated recombinant BAFF display similar binding properties.

Multi-array 96-well assay plates (Meso Scale Discovery, p/n. L15XA-3) are coated with 3.5 μg/mL of bispecific antibody and incubated overnight at 4° C. Following incubation, the plates are washed three times with PBS, then blocked using 3% Blocker A solution for 45 minutes at room temperature. The plates are then washed again with PBS. Exemplified bispecific antibody, starting at a concentration of 224 pM, is serially diluted (using 2-fold dilutions) in a V-bottom 96-well plate creating 12 different bispecific antibody concentrations. 7 pM of biotinylated recombinant BAFF is mixed with each dilution of exemplified bispecific antibody and then incubated at 37° C. for 36-48 hours (to reach equilibrium). Equilibrated samples are added to a well of the MSD multi-array 96-well assay plate previously coated with exemplified bispecific antibody; samples are mixed for 2.5 minutes, and then washed three times with PBS. Thereafter, 25 μL of 1 μg/mL SULFO-TAG labeled streptavidin detection reagent (Meso Scale Discovery, p/n. R32AD-5) in 1% Blocker A solution is added to each well. Plates are then incubated, on a plate shaker, at room temperature for 3 minutes and then washed with PBS. 1× Read Buffer T (Meso Scale Discovery, p/n. R92TC-1) is added to each well and plates are read on a MSDSI6000 plate reader (Meso Scale Discovery, Rockville Md.). Resulting binding signal reflects the amount of free antigen in solution. Data is exported to the KinExA Pro Software and results are fit to a "Standard, Affinity" binding model to determine $K_D$.

The binding affinity of the exemplified bispecific antibody to recombinant human BAFF (N=3), determined substantially as described herein, is $K_D$=0.3±0.4 μM (Avg.±SD). These results demonstrate that the exemplified bispecific antibody of the present invention produces a binding response (dependent upon the concentration of bispecific antibody) with human BAFF.

Simultaneous Binding of CD20 and BAFF

Flow cytometry is used to determine whether the exemplified bispecific antibody binds CD20 and BAFF simultaneously. Exemplified bispecific antibody and a control human IgG1 antibody are each fluorescently labeled with AlexaFlour488 (Life Technologies, p/n. A10468) according to manufacturer instructions. Recombinant human BAFF is biotinylated and serially diluted (using 5-fold dilutions) from 5000 ng to 0.32 ng.

The JY cell line is an Epstein-Barr virus immortalized human B cell lymphoblastoid line that expresses CD20 on the cell surface (ATCC 77442). JY cells are incubated for 30 minutes at 4° C. with each dilution of biotinylated BAFF and one of: a.) 1 μg of labeled exemplified bispecific antibody; or b.) 1 μg labeled control IgG1 antibody. Following incubation, cells are washed twice with FACS buffer (2% fetal bovine serum in PBS) and resuspended in FACS buffer for analysis. Both CD20 and BAFF binding is detected simultaneously via flow cytometry (Beckman Coulter FC500). CD20 binding is detected in the FL-1 (FITC) channel and BAFF binding is detected in the FL-2 (PE) channel. FACS data is analyzed by FCS Express 4 (De Novo Software). Results are presented in Table 2.

TABLE 2

Binding signal (Mean Fluorescence Intensity, MFI) of exemplified bispecific antibody to human CD20 and human BAFF in simultaneous binding assay.

| Biotinylated BAFF | Exemplified Bispecific Antibody (MFI) | | Control IgG1 Antibody (MFI) | |
|---|---|---|---|---|
| concentration (ng) | BAFF | CD20 | BAFF | CD20 |
| 5000 | 443.73 | 501.58 | 1.26 | 8.5 |
| 1000 | 30.76 | 916.18 | 1.3 | 9.14 |
| 200 | 5.42 | 895 | 1.43 | 18.02 |
| 0.32 | 1.43 | 1363.73 | 1.31 | 9.8 |

The results of Table 2 demonstrate that the exemplified bispecific antibody of the present invention is able to bind human CD20 on a cell surface and soluble BAFF, even at saturating concentrations of BAFF.

Neutralization of Soluble and Membrane-Bound BAFF-Induced Proliferation of T1165.17 Cells In Vitro T1165.17 cells are a BAFF-responsive murine cell line subcloned from T1165 murine plasmacytoma (derived from ascites tumors of BALB/c AnPt mice). Studies have shown T1165.17 cells require low levels of IL-1β, although in short-term proliferation assays other cytokines have been shown capable of substituting for IL-1β.

Soluble human BAFF (5 ng/mL) or membrane-bound human BAFF (18.1 ng/mL) are added to wells of a 96-well plate in triplicate. One of: a.) exemplified bispecific antibody; b.) parental BAFF antibody (such as described in U.S. Pat. No. 7,317,089); and c.) negative control antibody (IgG1 isotype antibody), is added to wells containing either soluble BAFF or membrane-bound BAFF at each of the following concentrations: 1.667, 0.556, 0.185, 0.062, 0.021, 0.007, and 0.002 (nM). T1165.17 cells are washed with serum free RPMI 1640 medium three times, then resuspended in assay medium containing RPMI 1640, 10% FBS, 1 mM sodium pyruvate, $5\times10^{-5}$ M 2-mercaptoethanol and an antibiotic/antimycotic (Gibco, p/n. 15240). The T1165.17 cells are added to each well at a concentration of 5000 cells/well and the plate is incubated for 44 hours at 5% $CO_2$ at 37° C. Following incubation, MTS Viability Substrate (Promega, p/n. G3580) is added to each well and the plate is incubated for an additional hour before an absorbance measurement at 490 nm on a microplate reader (Molecular Devises) is taken. Testing is carried out in triplicate.

TABLE 3a

Neutralization of soluble BAFF in vitro (compared to parental BAFF antibody and negative control antibody).

| | % Inhibition (Mean ± Std. Dev; N = 3) | | |
|---|---|---|---|
| Ab Concentration (nM) | Exemplified Bispecific Ab | Parental BAFF Ab | Negative Control Ab |
| 1.667 | 97.96 ± 1.00 | 97.88 ± 1.99 | −0.03 ± 3.40 |
| 0.556 | 99.20 ± 0.40 | 97.70 ± 4.96 | −0.42 ± 2.94 |
| 0.185 | 99.08 ± 0.99 | 96.86 ± 1.73 | −0.23 ± 5.86 |
| 0.062 | 96.97 ± 1.38 | 53.14 ± 10.58 | 1.83 ± 3.05 |
| 0.021 | 28.05 ± 1.87 | −1.36 ± 5.14 | 2.08 ± 0.76 |
| 0.007 | 9.50 ± 2.10 | −0.85 ± 3.53 | 3.50 ± 0.34 |
| 0.002 | 2.95 ± 1.86 | 1.52 ± 5.61 | 4.19 ± 1.77 |

TABLE 3b

Neutralization of membrane-bound BAFF in vitro (compared to parental BAFF antibody and negative control antibody).

| | % Inhibition (Mean ± Std. Dev; N = 3) | | |
|---|---|---|---|
| Ab Concentration (nM) | Exemplified Bispecific Ab | Parental BAFF Ab | Negative Control Ab |
| 1.667 | 100.94 ± 1.21 | 103.71 ± 0.61 | 0.87 ± 1.31 |
| 0.556 | 101.49 ± 0.44 | 103.93 ± 0.85 | 7.68 ± 4.26 |
| 0.185 | 98.49 ± 0.74 | 84.08 ± 3.07 | 1.12 ± 2.03 |
| 0.062 | 49.67 ± 1.74 | 18.06 ± 4.46 | 1.04 ± 2.16 |
| 0.021 | 11.48 ± 2.00 | 8.88 ± 3.67 | 1.98 ± 3.85 |
| 0.007 | 2.68 ± 3.21 | 7.99 ± 3.14 | 6.30 ± 9.33 |
| 0.002 | 1.98 ± 4.00 | 6.50 ± 4.41 | 4.13 ± 0.96 |

The results provided in Tables 3a and 3b demonstrate that the exemplified bispecific antibody of the present invention is able to completely neutralize (soluble and membrane-bound) BAFF-induced proliferation of T1165.17 cells. This neutralization is improved over the positive control antibody (parental BAFF antibody). Negative control IgG1 antibody does not demonstrate inhibition of either soluble or membrane-bound BAFF-induced proliferation of the T1165.17 cells.

In Vitro Analysis of Complement Dependent Cellular Cytotoxicity (CDC) Activity

Exemplified bispecific antibody and parental CD20 antibody (such as described in U.S. Pat. No. 8,153,125) are each respectively serially diluted (using 2-fold dilutions) from 10 μg/mL to 0.01 μg/mL. In order to assess if saturating amount of BAFF, when bound to the scFv portion of the exemplified bispecific antibody, impacts the CDC activity of the exemplified bispecific antibody each dilution is replicated in the presence and absence of saturating amounts (100 ng/mL) of soluble human BAFF trimer. Each dilution of both the exemplified bispecific antibody and parental CD20 antibody (with and without soluble human BAFF trimer) are added to WILS-2 B lymphoma cells (which express transmembrane CD20) plated on 96 well plates at a concentration of 40,000 cells/well and plates are incubated for 30 minutes at 37° C. Thereafter, purified human serum complement (Quidel, p/n. A133) at a dilution of 1:15 is added to each well and plates are incubated for 2 hours at 37° C. Following incubation, Alamar Blue (Biosource, p/n. DAL1100) is added to each well and plates are incubated overnight at 37° C. Relative Fluorescence Units (reflecting quantity of viable cells per well) is recorded at 540 nm excitation and 590 nm emission using a Molecular Devices Spectra Max Gemini EM Reader. Collected data is modeled to a 4-parameter fit sigmoidal dose response curve to calculate $EC_{50}$ values. Resulting $EC_{50}$ values are presented in Table 4.

TABLE 4

In Vitro Analysis of Complement Dependent Cellular Cytotoxicity in the Presence or Absence of Saturating BAFF.

| Measurement Model | $EC_{50}$ (nM) | |
|---|---|---|
| | Exemplified Bispecific Ab | Parental CD20 Ab |
| WIL2-S | 0.94 ± 0.04 (N = 2) | 0.83 ± 0.05 (N = 2) |
| WIL2-S + human BAFF | 1.17 ± 0.06 (N = 2) | 0.83 ± 0.07 (N = 2) |

The results provided in Table 4 demonstrate that the exemplified bispecific antibody of the present invention possesses CDC activity in the presence or absence of saturating amounts of soluble human BAFF, reducing the population of viable WIL2-S cells per well in a concentration dependent manner. The observed CDC activity of exemplified bispecific antibody is comparable to the parental CD20 antibody. The bispecific antibody of the present invention demonstrates effective CDC activity even with simultaneous engagement of BAFF.

In Vitro Analysis of Antibody Dependent Cellular Cytotoxicity (ADCC) Activity WIL2-S B lymphoma cells (which express human CD20), and human Jurkat T cells (ATCC #TIB-152) transduced with retroviral vectors to co-express NFAT-Luciferase Report Gene, gamma chain, and either a FcγIIIa (F158) receptor or a FcγIIIa (V158) receptor, are used to analyze ADCC activity of the bispecific antibody of the present invention. WIL2-S cells, at a concentration of 40,000 cells/well, are incubated for 1 hour at 37° C. with either exemplified bispecific antibody or parental CD20 antibody (such as described in U.S. Pat. No. 8,153,125), both of which have been serially diluted (using 3-fold dilutions) from 150 ng/mL to 0.07 ng/mL. Following incubation (1 hour at 37° C.) the transfected Jurkat T cells are added to the wells at a concentration of 200,000 cells/well and the plates are incubated for 3 hours at 37° C.

Luciferase reporter signal is generated by adding 100 μl of Steady Glo Luciferase substrate (Promega, p/n. E2520) to each well and mixing for 15 minutes. Reporter luminescent signal, indicating increased FcγIIIa receptor engagement (translating to increased ADCC activity) is measured using a SPECTRAmax LMaxII (Molecular Devices) and modeled to a 4-parameter fit sigmoidal dose response curve to calculate $EC_{50}$ values. Resulting $EC_{50}$ values are presented in Table 5 below.

TABLE 5

In Vitro Analysis of ADCC Activity.

| Measurement Model | $EC_{50}$ (pM) | |
|---|---|---|
| | Exemplified Bispecific Ab | Parental CD20 Ab |
| WIL2-S + Jurkat (V158) | 4.61 ± 0.34 (N = 2) | 5.05 ± 1.27 (N = 2) |
| WIL2-S + Jurkat (F158) | 31.35 ± 3.74 (N = 2) | 55.12 ± 5.90 (N = 2) |

The results provided in Table 5 demonstrate exemplified bispecific antibody of the present invention engages FcγIIIa receptors in a concentration dependent manner. The observed ADCC activity of exemplified bispecific antibody is comparable to the parental CD20 antibody. The exemplified bispecific antibody of the present invention demonstrates effective ADCC activity.

In order to assess if BAFF, when bound to the scFv portion of the bispecific antibody of the present invention, impacts the FcγIIIa receptor engagement (and ADCC) activity of the bispecific antibody of the present invention, the above experiment is reproduced (in duplicate) in the presence and absence of 1/3 serially diluted concentrations of soluble human BAFF trimer (from a starting concentration of 100 ng/mL). Parental CD20 antibody is tested in the absence of soluble human BAFF and at this highest starting concentration (100 ng/mL) of soluble human BAFF. Jurkat T cells transduced to co-express NFAT-Luciferase Report Gene and FcγIIIa (V158) receptor (as described above) are used. Resulting $EC_{50}$ data is presented in Table 6 below.

TABLE 6

In Vitro Analysis of ADCC Activity in the Presence of Saturating BAFF.

| Measurement Model [WIL2-S + Jurkat (V158)] | Exemplified Bispecific Ab $EC_{50}$ | Parental CD20 Ab $EC_{50}$ |
|---|---|---|
| no BAFF | 4.07 ± 0.64 (N = 2) | 5.91 ± 1.21 (N = 2) |
| 0.14 ng/mL BAFF | 4.71 ± 0.40 (N = 2) | N/A |
| 0.41 ng/mL BAFF | 5.15 ± 0.59 (N = 2) | N/A |
| 1.23 ng/mL BAFF | 7.68 ± 1.09 (N = 2) | N/A |
| 3.7 ng/mL BAFF | 11.61 ± 1.29 (N = 2) | N/A |
| 11.11 ng/mL BAFF | 15.23 ± 2.19 (N = 2) | N/A |
| 33.33 ng/mL BAFF | 16.08 ± 2.04 (N = 2) | N/A |
| 100 ng/mL BAFF | 15.81 ± 1.16 (N = 2) | 6.83 ± 1.22 (N = 2) |

The results provided in Table 6 demonstrate exemplified bispecific antibody of the present invention engages FcγIIIa receptors, even in the presence of BAFF. As shown in Table 6, exemplified bispecific antibody of the present invention experiences a slight reduction in FcγIIIa receptor engagement under saturating conditions of BAFF. The observed ADCC activity of exemplified bispecific antibody is slightly reduced compared to the parental CD20 antibody in the presence of saturating conditions of BAFF. The exemplified bispecific antibody of the present invention demonstrates effective ADCC activity during simultaneous engagement of BAFF.

In Vivo Analysis of BAFF Neutralization

Neutralization of human BAFF, in vivo, is assessed using transgenic FVB mice (FVB/N-TgN (LP40) 16989) which express human soluble BAFF. Human BAFF transgenic (Tg) mice are subcutaneously injected with 3.3 nmoles of: a.) exemplified bispecific antibody (N=5); b.) parental BAFF antibody (N=5); c.) human IgG4 negative control antibody (N=5); d.) parental CD20 antibody (N=5); or e.) untreated (naive mice, N=5). After eight days the mice are sacrificed and plasma and spleens are collected. Exposure of each antibody is confirmed by ELISA of plasma specific for human IgG.

A single cell suspension of spleen cells is prepared and the total number of leukocytes is determined following red blood cell lysis. The relative percentage of B lymphocytes is determined using cell surface marker B220 and flow cytometry, whereby the total number of B cells per spleen is able to be calculated by multiplying the percentage of B220 positive cells with the total number of leukocytes in the spleen. Results are presented in Table 7 below.

TABLE 7

B220 Positive Cells in Spleens of Treated Human BAFF Transgenic Mice (Mean + Std. Dev.).

|  | Naive (untreated) mice | Pos. Control Ab (parental BAFF Ab) | Exemplified Bispecific Ab | Neg. Control (parental CD20 Ab) | Neg. Control (IgG4 Ab) |
|---|---|---|---|---|---|
| B220+ Cells/ spleen ($\times 10^6$) | 176.46 ± 19.73 | 76.09 ± 24.16 | 52.98 ± 11.57 | 179.18 ± 31.61 | 152.53 ± 9.93 |

The results provided in Table 7 reflect a reduction in the total number of B cells in spleens of human BAFF Tg mice treated with a single subcutaneous injection of exemplified bispecific antibody as compared to naïve, negative control, and parental CD20 antibody treated transgenic mice. This reduction of B cells is equivalent to that observed with the parental BAFF antibody. The exemplified bispecific antibody of the present invention demonstrates effective in vivo neutralization of BAFF.

In Vivo Efficacy Models

The exemplified bispecific antibody of the present invention does not bind murine CD20 and has greatly reduced binding to murine BAFF (approximately a 250 fold reduction in binding to murine BAFF as compared to human BAFF). Additionally, a surrogate murine bispecific antibody was not able to be produced. Therefore, separate murine antibodies (one directed to murine CD20 and one directed to murine BAFF) are used for testing the therapeutic potential of dual targeting CD20 and BAFF in a rodent model.

Lupus-like autoimmunity is induced in host mice (female C57BL/6×DBA/2 F1 mice, Charles River Laboratories) via transfer of 14×10$^6$ CD4+ splenocytes from donor mice (7 to 8 week old female DBA/2 mice, Charles River Laboratories). CD4+ splenocytes from the donor mice are transferred into the tail vein of the host mice as described by Via CS and Shearer G M, Ann NY Acad. Sci., 532: 44-50 (1988). Upon transfer, donor CD4+ splenocytes provide cognate help to host B cells, resulting in proliferation/expansion of host B cells, including autoreactive host B cells.

In order to explore B cell depletion in the context of an ongoing immune response, CD4+ splenocytes are transferred from donor mice to host mice. Seven days post-transfer host mice are tested via ELISA for anti-dsDNA autoantibodies (as described below) to confirm initiation of disease. On day 7 post-transfer, host mice are also treated subcutaneously according to one of four treatment groups:

(a) 65 μg murine CD20 antibody+65 μg mIgG1 isotype control antibody (N=4);

(b) 65 μg murine BAFF antibody+65 μg mIgG1 isotype control antibody (N=4);

(c) 65 μg murine CD20 antibody+65 μg BAFF antibody (N=4); or (d) 130 μg mIgG1 isotype control antibody (N=4).

Host mice are sacrificed 7 days post-antibody treatment and B220+ cell values in blood, lymph node, and spleen are determined by flow cytometry as described above (in relation to splenic B cell levels of treated transgenic BAFF mice). Results are presented in Table 8 below.

TABLE 8

B220+ Cells in Blood, Lymph Node, and Spleens of Treated Host Mice (Mean + Std. Dev.).

|  | Naive Mice | (a) CD20 Ab + Control Ab | (b) BAFF Ab + Control Ab | (c) CD20 Ab + BAFF Ab | (d) Neg. Control (mIgG1 Ab) |
|---|---|---|---|---|---|
| B220+ Cells/μl blood | 5554 ± 1264 | 604 ± 220 | 3983 ± 1524 | 468 ± 124 | 3057 ± 1071 |
| B220+ Cells ($\times 10^6$)/lymph node | 0.59 ± 0.24 | 0.92 ± 0.39 | 1.91 ± 0.33 | 0.26 ± 0.04 | 4.40 ± 0.90 |
| B220+ Cells ($\times 10^6$)/spleen | 21.91 ± 8.79 | 21.94 ± 10.89 | 32.93 ± 6.61 | 5.97 ± 4.65 | 52.12 ± 18.55 |

The results provided in Table 8 demonstrate the total number of B cells in blood, lymph node, and spleen of host mice treated with a single subcutaneous injection of the murine CD20 antibody and murine BAFF antibody is significantly reduced over negative control treated mice. The level of B cells in host mice treated with murine CD20 antibody and murine BAFF antibody is reduced to levels below that of naïve mice and mice treated with only one of murine CD20 antibody or murine BAFF antibody alone.

In a 7 week study, CD4+ splenocytes are transferred from donor mice to host mice, and on the day of splenocyte transfer host mice are treated subcutaneously according to one of four treatment groups:
(a) 65 μg murine CD20 antibody+65 μg mIgG1 isotype control antibody (N=10);
(b) 65 μg murine BAFF antibody+65 μg mIgG1 isotype control antibody (N=10);
(c) 65 μg murine CD20 antibody+65 μg murine BAFF antibody (N=10); or
(d) 130 μg mIgG1 isotype control antibody (N=10).
Host mice are sacrificed 7 weeks post treatment and anti-dsDNA autoantibody presence and urine albumin/creatinine values are measured as described in detail below.

Anti-dsDNA autoantibody presence in host mice plasma samples is determined by ELISA. Greiner 96-well microtiter plates (Bellco Glass, p/n. 655 061) are coated with 10 μg/mL of Trevigen (R&D Systems, p/n. 9600-5D) calf thymus DNA in Dulbecco's phosphate buffered saline (D-PBS, no Mg, no Ca) and incubated overnight at 4° C. Following incubation, plates are blocked with D-PBS containing 2% bovine serum albumin (BSA) for 1 hour at room temperature (RT) then washed with 0.05% Tween 20 in PBS.

Plasma from host mice is collected on the day of sacrifice and plasma samples are diluted with 0.05 Tween 20 in PBS plus 2% BSA to a starting dilution of 1:100. Six 4-fold serial dilutions, from the starting 1:100 plasma dilution, are prepared for each plasma sample collected. Diluted plasma samples are added to individual wells of the plate and plates are incubated for 2 hours at room temperature, washed with 0.05% Tween 20 in PBS, and then incubated for 90 minutes with goat anti-mouse IgG (H and L)-HRP (Jackson ImmunoResearch, p/n. 115-035-166) diluted to a 1:2000 dilution with 0.05% Tween 20 in PBS plus 2% BSA. Thereafter, TMB substrate (Thermo Scientific, p/n. 34021) is added to each well. Color development is stopped with 0.5 M $H_2SO_4$. Colorimetric signal is read using a spectrophotometer at A450 (SpectraMax, Molecular Devices) and collected data is analyzed using a GraphPad Prism for determining anti-DNA titer ($EC_{50}$) values. Anti-dsDNA titer values are presented in Table 9.

Albumin/Creatinine ratios are a useful metric for assessing renal involvement relating to the progression of SLE. Albumin/Creatinine ratio values are determined by measuring both albumin (μg/mL) and creatinine (mg/dL) values, individually, in host mice urine according to the equation: [(urine albumin (μg/mL)/urine creatinine (mg/dL))× 100=Albumin Creatinine Ratio (μg/mg)]. Urine creatinine levels are measured with a Cobas CREA Plus assay (Roche, p/n. 11775685) according to manufacturer instructions.

Urine albumin levels are determined by sandwich ELISA. Microtiter plates (Greiner Bio-One, p/n. 655061) are coated with 60 μl of rabbit, anti-mouse albumin antibody (Acris Antibodies, p/n. AP09221PU-N) at a concentration of 0.75 μg/mL (diluted in PBS), then washed with washing buffer (20 mM Tris, 0.15 M NaCl, 0.1% Tween 20, pH 7.4) and blocked using blocking buffer (casein in PBS, Pierce Protein Biology Products, p/n. 37528). Urine samples are prepared by 1:2000 dilution and 1:80,000 dilution with blocking buffer (Pierce, p/n. 37528). A standard curve is generated by serially diluting a 200 ng/mL concentration of mouse albumin (Innovative Research, p/n. IMSA) down to 0.78 ng/mL using 1:2 dilutions of blocking buffer (Pierce, p/n. 37528). Standard curve serial dilutions (50 μL) and sample dilutions (50 μL) are added to individual wells of the plate in duplicate and incubated at room temperature for 1.5 hours. Thereafter, plates are washed with washing buffer, and then incubated at room temperature for 1 hour with 50 μL of a 1:3000 dilution of goat, anti-mouse albumin-HRP (Bethyl, p/n. A90-234P). Plates are washed with washing buffer, and then developed by addition of 50 μl of OPD substrate (Sigma, p/n. P-6912) to each well. The colorimetric reaction is stopped by addition of 100 μL of 1 N HCl. Colorimetric signal is measured at 490 nm using a plate reader (SpectraMax, Molecular

TABLE 9

Anti-dsDNA Titer Values (Mean + Std. Dev.).

| | Naïve Mice | (a) CD20 Ab + Control Ab | (b) BAFF Ab + Control Ab | (c) CD20 Ab + BAFF Ab | (d) mIgG1 Control Ab |
|---|---|---|---|---|---|
| Anti-dsDNA titer ($EC_{50}$) | 90 ± 44 | 3633 ± 4622 | 3160 ± 3535 | 35 ± 58 | 2692 ± 1780 |

The results provided in Table 9 demonstrate upon treatment with both murine CD20 antibody and murine BAFF antibody, anti-DNA titers are significantly lower than treatments with CD20 antibody alone or BAFF antibody alone.

Devices) and collected data is analyzed using SoftMax 3.1.2 software and a 4 parameter fit to back calculate sample concentrations. Albumin Creatinine Ratio values are presented in Table 10.

TABLE 10

Albumin Creatinine Ratio Values (Mean ± Std. Dev.).

| | Naïve Mice | (a) CD20 Ab + Control Ab | (b) BAFF Ab + Control Ab | (c) CD20 Ab + BAFF Ab | (d) mIgG1 Control Ab |
|---|---|---|---|---|---|
| ACR (μg/mg) | 9 ± 2 | 47211 ± 40805 | 26881 ± 36169 | 46 ± 113 | 14238 ± 12153 |

The results provided in Table 10 demonstrate a significant reduction in Albumin Creatinine Ratio of mice treated with both murine CD20 antibody and murine BAFF antibody, as opposed to mice treated with murine CD20 antibody alone or murine BAFF antibody alone.

Pharmacokinetic Assessment in Cynomolgus Monkey

The amino acid sequence of cynomolgus monkey shares 96.6% identify with the amino acid sequence of human CD20. Flow cytometry of cynomolgus monkey whole blood is used to confirm binding of the exemplified antibody to cynomolgus monkey CD20.

Whole blood (50 μL) collected from cynomolgus monkey is incubated at room temperature for 30 minutes with either: (a) exemplified bispecific antibody (1.5 μg) (labeled with AlexaFluor647) and positive control antibody (1.5 μg)(FITC labelled CD40 antibody reactive with cynomolgus monkey from BioLegend, p/n. 334306); or (b) human IgG1 isotype negative control antibody (1.5 μg)(labeled with AlexaFluor647) and positive control antibody (1.5 μg)(FITC labelled CD40 antibody reactive with cynomolgus monkey from BioLegend, p/n. 334306). Following incubation, red blood cells are lysed by addition of FACS Lysing Solution according to the manufacturer's instructions (Becton Dickinson & Co., p/n. 349202). Cells are washed three times with FACS buffer (PBS containing 2% fetal bovine serum), then resuspended in FACS buffer prior to flow cytometry using Beckman Coulter FC500. CD20 binding is detected in the FL-4 (647) channel and CD40 binding is detected in the FL-1 (FITC) channel Results are presented in Table 11 below.

TABLE 11

Binding of Exemplified Antibody to CD40+ Cynomolgus Monkey B Cells.

| | CD20 AlexaFluor647 (MFI) | CD40 FITC (MFI) |
|---|---|---|
| Exemplified Bispecific Ab + Pos. Control (CD40 Ab) | 588.21 | 139.49 |
| Neg. Control (human IgG1 Isotype Ab) + Pos. Control (CD40 Ab) | 171.88 | 148.55 |

The results provided in Table 11 demonstrate the exemplified bispecific antibody of the present invention binds cynomolgus monkey CD20 of B cells, whereas the human IgG1 negative control antibody does not bind the cynomolgus monkey B cells. These results support the use of cynomolgus monkey for in vivo testing of the bispecific antibody of the present invention.

In order to assess serum pharmacokinetics of the exemplified bispecific antibody, male cynomolgus monkeys are administered 13.3 mg/kg of exemplified bispecific antibody either intravenously (N=2) or subcutaneously (N=2). Exemplified bispecific antibody is prepared in solution of PBS, pH 7.4. Pharmacokinetic studies with a bispecific antibody comprising parental CD20 antibody and parental BAFF were not possible due to the physical and chemical instability (described herein) preventing expression and recovery.

Prior to administration, approximately 1.5 mL of blood is collected from each cynomolgus monkey. Post administration, blood samples (approximately 1.5 mL) are collected intravenously from a femoral vein into tubes serum separator tubes (e.g., containing no anticoagulant) at 1, 6, 12, 24, 48, 72, 96, 168, 240, 336, 432, 504, 600, and 672 hours post administration. Upon collection at the respective time points, samples are processed to serum.

Clearance of the exemplified bispecific antibody is determined by analysis of serum samples by total human IgG ELISA utilizing AffiniPure F(ab')$_2$ Fragment Goat Anti-Human IgG, F(ab')$_2$ fragment specific (Jackson ImmunoResearch Laboratories, Inc., p/n. 109-006-097) coated on ELISA plates (Thermo Scientific™ Immulon® 4HBX). Serum samples (100 μL), from each respective time point, are added to individual wells of ELISA plates and incubated at 25° C. for 60 mins. Following incubation, 100 μL (50,000 fold dilution) mouse anti-human IgG Fc-HRP (Southern Biotech, p/n. 9040-05) is added to wells of ELISA plate for detection of exemplified bispecific antibody. Unbound enzyme is removed via washing and 100 μL TMB Microwell Peroxidase Substrate System (KPL, p/n. 50-76-00) is added to individual wells of ELISA plate. Color development is stopped by addition of 100 μL TMB Stop Solution (KPL, p/n. 50-85-05) and optical density of the wells is measured at 450 nm with wavelength correction set to 630 nm.

A standard curve of known amounts of exemplified bispecific antibody, in 100% cynomolgus monkey serum (BioreclamationIVT, p/n. CYNSRM), for use in determination of clearance values is also generated. Exemplified bispecific antibody, in 100% cynomolgus monkey serum is diluted with 20-fold serial dilutions into blocker casein in PBS (Thermo Scientific™ Blocker™, p/n. 37528). The standard curve range of exemplified bispecific antibody is 78.1-5000 ng/mL (with an upper and lower limit of quantification of 1900 ng/mL and 120 ng/mL, respectively).

Clearance values for the exemplified bispecific antibody are calculated using immunoreactivity versus time profile from time zero (administration of antibody) to 192 hours post administration and are determined via non-compartmental analysis using Phoenix software (WinNonLin 6.3, Connect 1.3). Exemplified bispecific antibody administered intravenously demonstrates a mean clearance of 0.83 mL/hr/kg and a mean half-life of 58 hours. When administered subcutaneously, exemplified bispecific antibody demonstrates a mean clearance of 1.22 mL/hr/kg, a mean half-life of 72 hours and bioavailability of 69%. The results demonstrate that the exemplified bispecific antibody possess sufficient half-life, clearance, and bioavailability to support subcutaneous dosing.

Stability of the exemplified bispecific antibody in cynomolgus circulation is determined based on a ratio of BAFF antigen capture values (of serum samples collected at the time points described above) to total human IgG ELISA values (calculated as described above). BAFF antigen capture utilizes BAFF antigen (Eli Lilly and Company), which is coated on ELISA plates (Thermo Scientific™ Immulon® 4HBX). Serum samples (100 μL), from each respective time point described above, are added to individual wells of ELISA plates and incubated at 25° C. for 60 mins. Following incubation, 100 μL (10,000 fold dilution) mouse anti-human IgG Fc-HRP (Southern Biotech, p/n. 9040-05) is added to wells of ELISA plate for detection of exemplified bispecific antibody. Unbound enzyme is removed via washing, and 100 μL TMB Microwell Peroxidase Substrate System (KPL, p/n. 50-76-00) is added to individual wells of ELISA plate. Color development is stopped by addition of 100 μL TMB Stop Solution (KPL, p/n. 50-85-05) and optical density of the wells is measured at 450 nm with wavelength correction set to 630 nm.

Area under the curve (AUC) for both BAFF antigen capture and total human IgG ELISA are determined via non-compartmental analysis using Phoenix (WinNonLin 6.3, Connect 1.3). Mean percent area under the curve (% AUC) values are calculated as ($AUC_{0-tlast}$, BAFF antigen capture assay/AUC$_{0\text{-}tlast}$, total human IgG assay)*100%. The exemplified bispecific antibody demonstrates a % AUC, based on BAFF binding, of approximately 95% to 101%. The results reflect that the exemplified bispecific antibody possesses sufficient stability at both linkers L1 and L2.

Bispecific Antibody Physical and Chemical Property Analysis

Preliminary studies with a bispecific antibody comprising parental CD20 antibody and parental BAFF were not possible due to poor bispecific antibody expression, LC clipping, misfolding of scFv, poor purification recovery, bispecific antibody degradation/clipping, poor thermostability, and low affinity (relative to the parental antibodies). However, preliminary studies with the exemplified bispecific antibody of the present invention demonstrate unexpected beneficial properties, including expression of the bispecific antibody and unexpected beneficial chemical and physical stability and solubility properties. As demonstrated by the data provided herein, the bispecific antibody of the present invention exhibits low HMW aggregation, good solubility, good viscosity in solution, increased physical stability including low degradation levels and high photostability, low peptide bond cleavage, and both high and low concentration freeze thaw stability, while maintaining good affinity for both CD20 (as measured by FACS analysis described herein) and BAFF (as measured by ELISA analysis described herein), and maintaining neutralization activity of BAFF as well as ADCC activity (both analyzed as described herein).

Physical and Chemical Stability Analysis

For physical and chemical stability analysis, the exemplified bispecific antibody of Table 1 is formulated in 10 mM acetate pH 5.0, 0.02% Tween-80. Exemplified bispecific antibody samples are concentrated to 1 mg/mL, 50 mg/mL and 100 mg/mL (using Amicon U.C. filters, Millipore, p/n. UFC903024).

Sample stability, of samples concentrated to 1 mg/mL is assessed by incubating samples at one of 4, 25, and 40° C. over a period of 4 weeks. Samples concentrated to 50 and 100 mg/mL are incubated in the presence and absence of 150 mM NaCl at one of 4 and 25° C. over a period of 4 weeks.

Following the respective incubation periods, samples are analyzed for percent high molecular weight (% HMW) with size exclusion chromatography (SEC) using a TSK G3000SW (Tosoh Bioscience, p/n. 08541) column. 50 mM sodium phosphate+350 mM NaCl, pH 7.0 is used as the mobile phase running at 0.5 mL/min for 35 mins A volume of 10 μL (10 μg) of the 1 mg/mL antibody sample is injected into the column and the detection is measured at 214 nm. For high concentration samples, a volume of 1 μL (50 μg or 100 μg) is injected into the column and the detection is measured at 280 nm Chromatograms are analyzed using ChemStation and % high molecular weight (HMW) is calculated using the ratio of AUC of the peaks eluted before the monomer peak to total AUC. Results are summarized in Table 12.

TABLE 12

Change in % high molecular weight species from starting control over 4 weeks measured by SEC.

| Sample Concentration | Incubation Temperature | Change in % of HMW |
|---|---|---|
| 1 mg/mL | 4° C. | 0.27 |
| 1 mg/mL | 25° C. | 0.24 |
| 1 mg/mL | 40° C. | 0.28 |
| 50 mg/mL | 4° C. | 0.73 |

TABLE 12-continued

Change in % high molecular weight species from starting control over 4 weeks measured by SEC.

| Sample Concentration | Incubation Temperature | Change in % of HMW |
|---|---|---|
| 50 mg/mL | 25° C. | 0.81 |
| 100 mg/mL | 4° C. | 0.97 |
| 100 mg/mL | 25° C. | 1.38 |

The results provided in Table 12 demonstrate the exemplified bispecific antibody of the present invention, formulated as described herein, achieves high protein concentrations and displays less than a 1.4% change in high molecule weight content following a four week degradation study of 25° C.

Sample degradation, of samples concentrated to 1 mg/mL, is also analyzed with capillary isoelectric focusing (cIEF) analysis using a Beckman-PA800 plus system according to manufacturer instructions. For samples incubated at 4° C., the percent sample degradation was measured as 0%; for samples incubated at 25° C. the percent sample degradation was measured as 1.3%.

Samples concentrated to 1 mg/mL and stored at 40° C. are also analyzed for identification of peptide bond cleavage with liquid chromatography-mass spectrometry (LC-MS) analysis using a Thermo Scientific Ion Trap LC-MS system according to manufacturer instructions. No region of the bispecific antibody demonstrated peptide bond cleavage of greater than 2% and the hinge region (of the first polypeptide chain, SEQ ID NO:1 of the exemplified bispecific antibody) demonstrated peptide bond cleavage of only approx. 1%.

Solubility Analysis

Solubility of the exemplified bispecific antibody is analyzed at 4, −5 and −10° C. following a one week incubation period at each temperature. Solubility is assessed with bispecific antibody samples concentrated to between 100 and 150 mg/mL (using Amicon U.C. filters, Millipore, catalog # UFC903024) and formulated in 10 mM acetate at pH 5.0. The exemplified bispecific antibody exhibited solubility of at least 148 mg/mL, within acceptable values for therapeutic bispecific antibodies. The exemplified bispecific antibody also demonstrated only a 0.49% change in the level of HMW content at high concentration, and lacked phase separation following the incubation period. Viscosity of the exemplified bispecific antibody is analyzed at room temperature.

Viscosity is assessed with bispecific antibody concentrated to 100 mg/mL and formulated in 10 mM acetate at pH 5.0. The exemplified bispecific antibody exhibited viscosity of 4.9 cp at 100 mg/mL, an acceptable value for therapeutic bispecific antibodies.

Photostability Analysis

Photostability analysis of the exemplified bispecific antibody is assessed with bispecific antibody concentrated at 50 mg/mL and formulated in either: (a) 10 mM acetate, pH 5.0, 0.02% Tween-80; or (b) 10 mM citrate, pH 6.0, 0.02% Tween-80, 150 mM NaCl. Samples are exposed for 240,000 lux hour visible light plus 40 watt-hr/m$^2$ UV light. Control ("dark") samples are not exposed to light. Samples are then analyzed on a size exclusion chromatography (SEC) using a TSKgel Super G3000SW column Results are summarized in Table 13.

TABLE 13

Summary of change in percentage of high molecular weight species.

| Sample Formulation (50 mg/mL) | Change in % of HMW compared to control samples |
|---|---|
| (a) 10 mM acetate, pH 5.0, 0.02% Tween-80 | <3% |
| (b) 10 mM citrate, pH 6.0, 0.02% Tween-80, 150 mM NaCl | between 7-10% |

The results provided in Table 13 demonstrate the exemplified bispecific antibody of the present invention, formulated in 10 mM acetate, pH 5.0, 0.02% Tween-80 at high concentrations, possesses photostability comparable to other therapeutic bispecific antibodies.

High and Low Concentration Freeze/Thaw Analysis

Freeze thaw analysis of exemplified bispecific antibody of the present invention is assessed following three freeze/thaw cycles performed according to Table 14:

TABLE 14

One Cycle of a Freeze Thaw Analysis.

| Cycle Step | 1 | 2 | 3 | 4 | 5 | 6 | 7 | 8 |
|---|---|---|---|---|---|---|---|---|
| Target Temp. (° C.) | 5 | −1 | −30 | −70 | −30 | −1 | 0.5 | 15 |
| Temp. Rate (° C./min.) | 1 | 0.05 | 0.2 | 1 | 1 | 0.2 | 0.2 | 1 |
| Hold (min.) | 10 | 750 | 1 | 60 | 1 | 1000 | 1 | 1 |

Low concentration freeze/thaw analysis of the exemplified bispecific antibody is assessed with bispecific antibody concentrated at 1 mg/mL and formulated in 10 mM acetate, pH 5.0, with and without 0.02% Tween-80. Three freeze/thaw cycles (a single cycle represented in Table X) are performed and particle growth for each sample is assessed using a HIAC Particle Counter (Pacific Scientific, p/n. 9703). Particle counts for both formulations (with and without 0.02% Tween-80) were less than or equal to 100. Formulations with 0.02% Tween-80 demonstrated no difference in particle counts in comparison to control samples not subjected to freeze/thaw cycles, demonstrating the exemplified bispecific antibody of the present invention, under low concentration conditions, is stabile following multiple freeze/thaw cycles.

High concentration freeze/thaw analysis of the exemplified bispecific antibody is assessed with bispecific antibody concentrated at 50 mg/mL and formulated in either: (a) 10 mM acetate, pH 5.0, 0.02% Tween-80; or (b) 10 mM citrate, pH 6.0, 0.02% Tween-80, with and without 150 mM NaCl. Three freeze/thaw cycles (a single cycle represented in Table X) are performed and particle growth for each sample is assessed using a HIAC Particle Counter. Results are provided in Table 15:

TABLE 15

Particle Count Following High Concentration Freeze/Thaw.

| | (a) 10 mM acetate, pH 5.0, 0.02% Tween-80 | (b) 10 mM citrate, pH 6.0, 0.02% Tween-80 +150 mM NaCl | (b) 10 mM citrate, pH 6.0, 0.02% Tween-80 −150 mM NaCl |
|---|---|---|---|
| 0 Freeze/Thaw Cycles | 118 | 66 | 90 |
| 3 Freeze Thaw Cycles | 104 | 1728 | 1786 |

The results provided in Table 15 demonstrate the exemplified bispecific antibody of the present invention at high concentrations and formulated in 10 mM acetate, pH 5.0, 0.02% Tween-80, is stabile following multiple freeze/thaw cycles.

Sequences

First Polypeptide of the exemplified bispecific antibody of Table 1

(SEQ ID NO: 1)

QVQLQESGPGLVKPSETLSLTCTVSGGSFSGHYWSWIRQPPGKCLEWIGE

INHSGSTNYNPSLKSRVTISVDTSKNQFSLKLSSVTAADTAVYYCARGAR

DILTGYLYYYDHWGQGTLVTVSSGGGGSGGGGSGGGGSGGGGSEIVLTQS

PATLSLSPGERATLSCRASQVSRYLAWYQQKPGQAPRLLIYDASNRATGI

PARFSGSGSGTDSTLTISSLEPEDFAVYYCQQRSNHPRTFGCGTKVEIKG

GGGSGGGGSGGGGSEVQLVQSGAEVKKPGESLKISCKGSGRTFTSYNMHW

VRQMPGKGLEWMGAIYPLTGDTSYNQKSKLQVTISADKSISTAYLQWSSL

KASDTAMYYCARSTYVGGDWQFDVWGKGTTVTVSSASTKGPSVFPLAPSS

KSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPE

EKTISKQKGQPREPQVYTLPPSRDELTKNQVSLTCLVKGFYPSDIAVEWE

SNGQPENNYKTTPPVLDSDGSFFLYSKLTVDKSRWQQGNVFSCSVMHEAL

HNHYTQKSLSLSPG

Second Polypeptide of the exemplified bispecific antibody of Table 1

(SEQ ID NO: 2)

EIVLTQSPGTLSLSPGERATLSCRASSSVPYIHWYQQKPGQAPRLLIYAT

SALASGIPDRFSGSGSGTDFTLTISRLEPEDFAVYYCQQWLSHPPTFGQG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC

DNA Seq. Encoding the First Polypeptide of the exemplified bispecific antibody of Table 1

(SEQ ID NO: 3)

caggtgcagctgcaggagtcgggcccaggactggtgaagccacggagacc ctgtccctcacctgcactgtctctggaggctccttcagtggtcattactg gagctggattcgccagcccccagggaagtgtctggagtggattggggaaa

```
tcaatcatagtggaagcaccaactacaacccgtccctcaagagtcgagtc
accatatcagtagacacgtccaagaaccagttctccctgaaactgagctc
tgtgaccgccgcggacacggctgtgtattactgtgcgagaggggctagag
atattagactggttatctatactactatgaccattggggccaggaaccc
tggtcaccgtctcctcaggggagggggcagcggaggaggcggatcgggc
ggaggaggaagtggaggcggaggcagcgaaattgtgagacgcagtctcca
gccaccctgtctagtctcctggggaaagagccaccctctcctgcagggcc
agtcagagtgttagccgctacttagcctggtaccagcagaaacctggcca
ggctcccaggctcctcatctatgatgcatccaacagggccactggcatcc
cagccaggacagtggcagtgggtctgggacagactccactctcaccatca
gcagcctagagcctgaagattagcagatattactgtcagcagcgtagcaa
ccaccctcggacgttcggctgtgggaccaaggtggaaatcaaaggcggtg
gtggcagcggcggaggcggatccggcggaggtggaagcgaggtgcagctg
gtgcagtctggagcagaggtgaaaaagcccggggagtctctgaagatctc
ctgtaagggactggccgtacatttaccagttacaatatgcactgggtgcg
ccagatgcccgggaaaggcctggagtggatgggggctatttatcccttga
cggtgatacttcctacaatcagaagtcgaaactccaggtcaccatctca
gccgacaagtccatcagcaccgcctacctgcagtggagcagcctgaaggc
ctcggacaccgccatgtattactgtgcgagatcgacttacgtgggcggtg
actggcagttcgatgtctggggcaaggggaccacggtcaccgtctcctca
gcctccaccaagggcccatcggtcttccccgctagcacccctcctccaagag
cacctctgggggcacagcggccctgggctgcctggtcaaggactacttcc
ccgaaccggtgacggtgtcgtggaactcaggcgccctgaccagcggcgtg
cacaccttcccggctgtcctacagtcctcaggactctactccctcagcag
cgtggtgaccgtgccctccagcagcagggcacccagacctacatctgcaa
cgtgaatcacaagcccagcaacaccaaggtggacaagaaagttgagccca
aatcagtgacaaaactcacacatgcccaccgtgcccagcacctgaactcc
tgggggggaccgtcagtatcctcaccccccaaaacctaaggacaccctcat
gatctcccggacccctgaggtcacatgcgtggtggtggacgtgagccacg
aagaccctgaggtcaagttcaactggtacgtggacggcgtggaggtgcat
aatgccaagacaaagccgcgggaggagcagtacaacagcacgtaccgtgt
ggtcagcgtcctcaccgtcctgcaccaggactggctgaatggcaaggagt
acaagtgcaaggtctccaacaaagccctcccagcccccgaggagaaaacc
atctccaaacagaaagggcagccccgagaaccacaggtgtacaccctgcc
cccatcccgggacgagctgaccaagaaccaggtcagcctgacctgcctgg
tcaaaggcactatcccagcgacatcgccgtggagtgggagagcaatggc
agccggagaacaactacaagaccacgccccccgtgctggactccgacggc
tcatcacctctatagcaagctcaccgtggacaagagcaggtggcagcagg
ggaacgtcactcatgctccgtgatgcatgaggctctgcacaaccactaca
cacagaagagcctctccctgtctccgggt DNA Seq. Encoding the Second Polypeptide of the
exemplified bispecific antibody of Table 1
                                      (SEQ ID NO: 4)
gaaattgtgttgacgcagtctccaggcaccctgtctttgtctccagggga
aagggccaccctctcctgcagggccagtcaagtgtaccgtacatccact
ggtaccagcagaaacctggccaggctcccaggctcctcatctatgccaca
tccgccctggcactggcatcccagacaggacagtggcagtgggtctggga
cagacttcactctcaccatcagcagactggagcctgaagattagcagtgt
attactgtcagcagtggctgagtcatccaccccacttaggccaggggacca
agctggagatcaaacgaactgtggctgcaccatctgtcacatcttcccgc
catctgatgagcagttgaaatctggaactgcctctgagtgtgcctgctga
ataacttctatcccagagaggccaaagtacagtggaaggtggataacgcc
ctccaatcgggtaactcccaggagagtgtcacagagcaggacagcaagga
cagcacctacagcctcagcagcaccctgacgctgagcaaagcagactacg
agaaacacaaagtctacgcctgcgaagtcacccatcagggcctgagctcg
cccgtcacaaagagcttcaacaggggagagtgc HCVR1 of the exemplified bispecific antibody of
Table 1
                                      (SEQ ID NO: 5)
QVQLQESGPGLVKPSETLSLTCTVSGGSFSGHYWSWIRQPPGKCLEWIGE
INHSGSTNYNPSLKSRVTISVDTSKNQFSLKLSSVTAADTAVYYCARGAR
DILTGYLYYYDHWGQGTLVTVSS HCVR2 of the exemplified bispecific antibody of
Table 1
                                      (SEQ ID NO: 6)
EVQLVQSGAEVKKPGESLKISCKGSGRTFTSYNMHWVRQMPGKGLEWMGA
IYPLTGDTSYNQKSKLQVTISADKSISTAYLQWSSLKASDTAMYYCARST
YVGGDWQFDVWGKGTTVTVSS LCVR1 of the exemplified bispecific antibody of
Table 1
                                      (SEQ ID NO: 7)
EIVLTQSPGTLSLSPGERATLSCRASSSVPYIHWYQQKPGQAPRLLIYAT
SALASGIPDRFSGSGSGTDFTLTISRLEPEDFAVYYCQQWLSHPPTFGQG
TKLEIK LCVR2 of the exemplified bispecific antibody of
Table 1
                                      (SEQ ID NO: 8)
EIVLTQSPATLSLSPGERATLSCRASQSVSRYLAWYQQKPGQAPRLLIYD
ASNRATGIPARFSGSGSGTDSTLTISSLEPEDFAVYYCQQRSNHPRTFGC
GTKVEIK HCDR1 of the exemplified bispecific antibody of
Table 1
                                      (SEQ ID NO: 9)
KGSGRTFTSYNMH HCDR2 of the exemplified bispecific antibody of
Table 1
                                      (SEQ ID NO: 10)
AIYPLTGDTSYNQKSKL HCDR3 of the exemplified bispecific antibody of
Table 1
                                      (SEQ ID NO: 11)
ARSTYVGGDWQFDV HCDR4 of the exemplified bispecific antibody of
Table 1
                                      (SEQ ID NO: 12)
TVSGGSFSGHYWS HCDR5 of the exemplified bispecific antibody of
Table 1
```

-continued

HCDR6 of the exemplified bispecific antibody of Table 1

(SEQ ID NO: 13)
EINHSGSTNYNPSLKS

HCDR6 of the exemplified bispecific antibody of Table 1

(SEQ ID NO: 14)
ARGARDILTGYLYYYDH

LCDR1 of the exemplified bispecific antibody of Table 1

(SEQ ID NO: 15)
RASSSVPYIH

LCDR2 of the exemplified bispecific antibody of Table 1

(SEQ ID NO: 16)
YATSALAS

LCDR3 of the exemplified bispecific antibody of Table 1

(SEQ ID NO: 17)
QQWLSHPPT

LCDR4 of the exemplified bispecific antibody of Table 1

(SEQ ID NO: 18)
RASQSVSRYLA

LCDR5 of the exemplified bispecific antibody of Table 1

(SEQ ID NO: 19)
YDASNRAT

LCDR6 of the exemplified bispecific antibody of Table 1

(SEQ ID NO: 20)
QQRSNHPRT

Polypeptide Linker 1 of the exemplified bispecific antibody of Table 1

(SEQ ID NO: 21)
GGGGSGGGGSGGGGSGGGGS

Polypeptide Linker 2 of the exemplified bispecific antibody of Table 1

(SEQ ID NO: 22)
GGGGSGGGGSGGGGS

---

We claim:

1. A bispecific antibody comprising two first polypeptide chains and two second polypeptide chains, wherein the amino acid sequence of each of said first polypeptide chains is SEQ ID NO:1 and the amino acid sequence of each of said second polypeptide chains is SEQ ID NO:2.

2. A pharmaceutical composition comprising a bispecific antibody and one or more pharmaceutically acceptable carriers, diluents, or excipients, wherein the bispecific antibody comprises two first polypeptide chains and two second polypeptide chains, wherein the amino acid sequence of each of said first polypeptide chains is SEQ ID NO:1 and the amino acid sequence of each of said second polypeptide chains is SEQ ID NO:2.

* * * * *